United States Patent [19]

Gandolfi et al.

[11] 4,169,145

[45] Sep. 25, 1979

[54] ω-NOR-CYCLOALKYL-13,14-DEHYDRO-PROSTAGLANDINS

[75] Inventors: Carmelo Gandolfi; Renato Pellegata; Roberto Ceserani; Maria M. Usardi, all of Milan, Italy

[73] Assignee: Carlo Erba S.p.A., Milan, Italy

[21] Appl. No.: 835,224

[22] Filed: Sep. 21, 1977

Related U.S. Application Data

[60] Continuation of Ser. No. 734,629, Oct. 21, 1976, abandoned, which is a division of Ser. No. 603,015, Aug. 8, 1975, Pat. No. 4,035,415.

[30] Foreign Application Priority Data

Sep. 25, 1974 [GB] United Kingdom ............... 27654/74

[51] Int. Cl.² .................... A61K 31/19; A61K 31/34; C07C 61/38; C07D 307/54

[52] U.S. Cl. .......................... 424/244; 549/9; 549/13; 549/79; 549/88; 549/90; 260/239 A; 260/239 E; 260/239 BF; 260/326.2; 260/326.46; 260/333; 260/345.7 P; 260/345.8 P; 260/347.3; 260/347.4; 260/347.5; 260/348.58; 424/267; 424/274; 424/275; 424/283; 424/285; 424/305; 424/308; 424/311; 424/317; 546/238; 560/107; 560/116; 560/117; 560/256; 562/498; 562/499

[58] Field of Search ........ 260/239 A, 239 E, 239 BF, 260/293.65, 326.2, 326.46, 327 R, 327 E, 332.2 A, 333, 345.7 P, 345.8 P, 347.3, 347.4, 347.5, 348.58, 514 D; 424/305, 308, 311, 317, 244, 267, 274, 275, 283, 285; 560/107, 116, 117, 256; 546/238; 562/498, 499

[56] References Cited

U.S. PATENT DOCUMENTS

| | | | |
|---|---|---|---|
| 3,876,690 | 4/1975 | Floyd et al. | 260/514 D |
| 3,884,969 | 5/1975 | Schaub et al. | 260/514 D |
| 3,935,254 | 1/1976 | Gandolfi et al. | 260/514 D |

Primary Examiner—Richard Raymond
Attorney, Agent, or Firm—Cushman, Darby & Cushman

[57] ABSTRACT

ω-nor-cycloalkyl-13,14-dehydro-prostaglandin compounds, specifically 13,14-dehydro-17-cyclohexyl-20,19,18-trinor-PGF$_{2\alpha}$ having antiulcer and luteolytic activity, are disclosed.

6 Claims, No Drawings

ω-NOR-CYCLOALKYL-13,14-DEHYDRO-PROSTAGLANDINS

CROSS-REFERENCE TO RELATED APPLICATIONS

This is a continuation of our copending application Ser. No. 734,629 filed Oct. 21, 1976, now abandoned which in turn is a divisional of our earlier application Ser. No. 603,015 filed Aug. 8, 1975, now U.S. Pat. No. 4,035,415.

The present invention relates to ω-nor-cycloalkyl-13,14-dehydro-prostaglandins, to a method for their preparation and to pharmaceutical compositions containing them.

The compounds of the invention are optically active or racemic prostaglandins of formula (I)

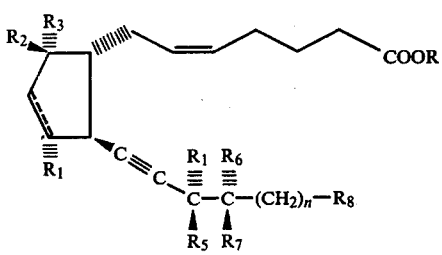

wherein

R is a hydrogen atom, a $C_1$-$C_{12}$ alkyl group or a cation of a pharmaceutically acceptable base;

the symbol --- represents a single or a double bond, wherein, when the symbol --- is a double bond, $R_1$ is a hydrogen atom, and $R_2$ and $R_3$ together form an oxo group, while, when the symbol --- is a single bond, $R_1$ is hydroxy, $R_2$ is hydrogen and $R_3$ is hydroxy or a carboxylic acyloxy or $R_2$ and $R_3$, taken together, form an oxo group; one of $R_4$ and $R_5$ is hydroxy and the other is hydrogen; $R_6$ and $R_7$ are independently hydrogen or $C_1$-$C_4$ alkyl; n is zero, 1, 2 or 3;

$R_8$ is a radical

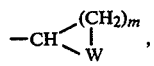

wherein m is 1, 2, 3, 4 or 5 and W is —$CH_2$—, an oxygen atom, a sulphur atom or a radical >$NR_9$, wherein $R_9$ is hydrogen or $C_1$-$C_4$ alkyl, or $R_8$ is 1-adamantyl, 2-norbornyl, 2-bicyclo[2,2,2]-octyl or 4-t.butyl-cyclohexyl.

The double bond in the 5(6)-position is a cis-double bond.

In the formulae of this specification, the broken lines (⫼⫼⫼⫼) indicate that the substituents are in the α-configuration, i.e. are below the plane of the ring or of the chain, while the heavy solid lines (◂) indicate that the substituents are in the β-configuration, i.e. above the plane of the ring or of the chain; the wavy line attachment (ξ) indicates that the groups may be either in the α-configuration, i.e. below the plane of the ring, or in the β-configuration, i.e. above the plane of the ring.

As is evident from formula (I), the hydroxy group linked to the carbon atom in the 15-position may be either in the α-configuration

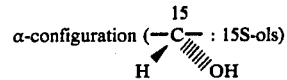

or in the β-configuration

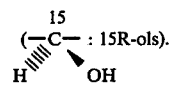

When on the carbon atom in the 16-position there is only one $C_1$-$C_4$ alkyl group, said substituent may be either a 16S-alkyl (α-configuration) or a 16R-alkyl (β-configuration) or a 16(S,R)-alkyl, i.e. the mixture of the two 16S- and 16R-diastereoisomers.

It is also evident that when the symbol --- represents a double bond and therefore $R_1$ is a hydrogen atom, this hydrogen atom, being linked to a carbon atom which is no more asymmetric, may be obviously in an only one fixed position, i.e. on the plane of the ring, and therefore it may be neither in the α-position (i.e. below the plane of the ring) nor in the β-position (i.e. above the plane of the ring).

The alkyl groups may be branched or straight chain groups.

When R is a $C_1$-$C_{12}$ alkyl group, it is preferably a methyl, ethyl or heptyl group; n is preferably 1.

When $R_6$ and $R_7$ are $C_1$-$C_4$ alkyl, the alkyl group is preferably methyl.

When in the radical

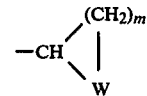

W is —$CH_2$—, said radical is preferably cyclopentyl, cyclohexyl or cycloheptyl; when W is an oxygen or a sulphur atom or a >$NR_9$ radical, m is preferably 3.

When $R_8$ is a 4-t.butyl-cyclohexyl radical, said radical may be either an endo or a hexo radical.

When $R_3$ is a carboxylic acyloxy group, it is preferably acetoxy, propionyloxy, benzoyloxy.

Examples of cations of pharmaceutically acceptable bases are either metallic cations, such as sodium, potassium, calcium, and aluminium or organic amine cations, such as trialkylamines.

The nor-compounds are those wherein n is 3; the dinor-compounds are those wherein n is 2; the trinor-compounds are those wherein n is 1, and the tetranor-compounds are those wherein n is zero.

Examples of preferred compounds of the invention are the following:

5c-9α,11α,15S-trihydroxy-20,19,18-trinor-17-cyclohexyl-prost-5-en-13-ynoic acid;

5c-9α,11α,15S-trihydroxy-20,19,18-trinor-17-cycloheptyl-prost-5-en-13-ynoic acid;

5c-9α,11α,15S-trihydroxy-20,19,18-trinor-17-cyclopentyl-prost-5-en-13-ynoic acid;

5c-9α,11α,15S-trihydroxy-20,19,18-trinor-17-cyclohexyl-prost-5-en-13-ynoic acid-9α-propionate;

5c-9α,11α,15S-trihydroxy-20,19-dinor-18-cyclohexyl-prost-5-en-13-ynoic acid;

5c-9α,11α,15S-trihydroxy-20,19,18,17-tetranor-16-cyclohexyl-prost-5-en-13-ynoic acid;

5c-9-oxo-11α,15S-dihydroxy-20,19,18-trinor-17-cyclohexyl-prost-5-en-13-ynoic acid;

5c-9-oxo-11α,15S-dihydroxy-20,19,18-trinor-17-cyclohexyl-16S-methyl-prost-5-en-13-ynoic acid;

5c-9-oxo-11α,15S-dihydroxy-20,19,18-trinor-17-cyclohexyl-16R-methyl-prost-5-en-13-ynoic acid.

The compounds of general formula (I) may be prepared by a process comprising reacting an optically active compound, or a racemic mixture of compounds, of general formula (II)

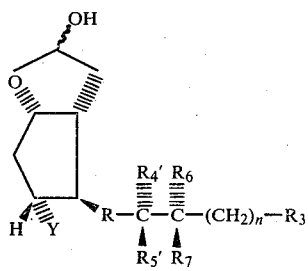

wherein B may be —C≡C— or

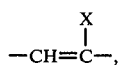

wherein X is bromine, chlorine or iodine, and wherein $R_6$, $R_7$, $R_8$ and n are as defined above, one of $R'_4$ and $R'_5$ is a hydroxy or a known protecting group bound to the chain by an ethereal oxygen atom, and the other is a hydrogen atom, Y is a hydroxy or a known protecting group bound to the ring by an ethereal oxygen atom, with a Wittig reagent comprising a group of formula —(CH$_2$)$_4$—COOR, wherein R is a hydrogen atom or a $C_1$-$C_{12}$ alkyl group, to give a compound of general formula (III)

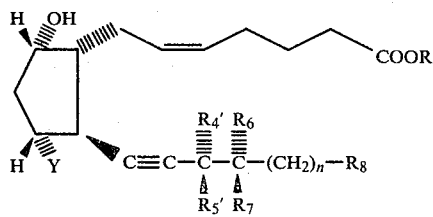

wherein R, Y, $R'_4$, $R'_5$, $R_6$, $R_7$, $R_8$ and n are as defined above, which, when Y is a known protecting group as above defined, and one of $R'_4$ and $R'_5$ is a known protecting group as above defined and the other is hydrogen, may be optionally esterified to give the 9α-acyloxy derivative, and then, deetherifying the compound of formula (III) wherein Y is a known protecting group as above defined and/or one of $R'_4$ and $R'_5$ is a known protecting group as above defined and the other is hydrogen, or deetherifying the 9α-acyloxy derivative of the compound of formula (III), so obtaining a compound of formula (I), wherein $R_1$ is a hydroxy group, the symbol---is a single bond, $R_2$ is hydrogen and $R_3$ is hydroxy or a carboxylic acyloxy, and one of $R_4$ and $R_5$ is a hydroxy group and the other is hydrogen, or, if desired, oxidizing the 9α-hydroxy group in the compound of formula (III) wherein Y is a known protecting group as above defined, and one of $R'_4$ and $R'_5$ is a known protecting group as above defined and the other is hydrogen, to give a compound of general formula (IV)

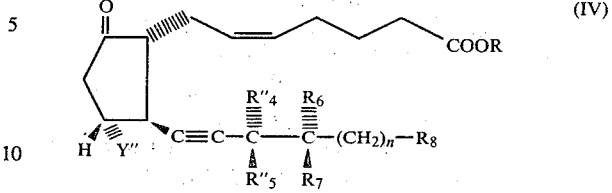

wherein R, $R_6$, $R_7$, $R_8$ and n are as above-defined, Y″ is a known protecting group as defined above, and one of $R''_4$ and $R''_5$ is a known protecting group as defined above and the other is hydrogen, which, in turn, is deetherified in the 11- and 15-positions to give, according to the reaction conditions used, either a compound of general formula (I) wherein the symbol---is a single bond, $R_1$ is hydroxy, and $R_2$ and $R_3$ taken together form an oxo group, or a compound of general formula (I) wherein the symbol---is a double bond, $R_1$ is hydrogen and $R_2$ and $R_3$ together form an oxo group, and then, if desired, reacting a compound of general formula (I) wherein R is a hydrogen atom with a base to give a compound of general formula (I) wherein R is a cation, or esterifying a compound of general formula (I) wherein R is a hydrogen atom, to give a compound of general formula (I) wherein R is $C_1$-$C_{12}$ alkyl, or hydrolysing a compound of general formula (I) wherein R is $C_1$-$C_{12}$ alkyl, to give a compound of general formula (I) wherein R is a hydrogen atom.

The hydrolysis of a compound of formula (I) wherein $R_2$ and $R_3$ together form an oxo group, and wherein R is $C_1$-$C_{12}$ alkyl, to give a compound of formula (I) wherein $R_1$ and $R_2$ together form an oxo group and R is hydrogen may be also carried out by enzymatic way, e.g. by using a yeast esterase.

The known protecting groups (i.e. ether groups) should be convertible to hydroxy groups under mild reaction conditions, e.g. acid hydrolysis. Examples are acetalic ethers, enol-ethers and sylylethers. The preferred groups are

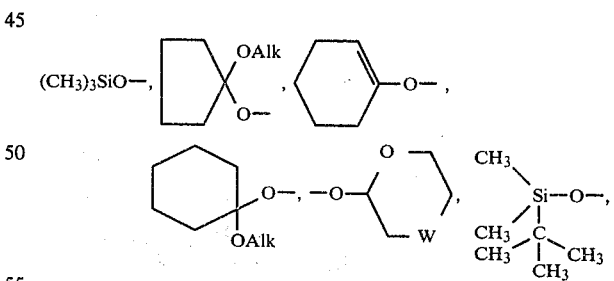

wherein W is —O— or —CH$_2$—, and Alk is a lower alkyl group.

When in the lactol of formula (II) B is —C≡C— or

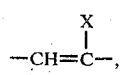

wherein X is bromine or iodine, the Wittig reaction may be performed using about two moles of Wittig reagent per mole of lactol and it is sufficient that the reaction lasts 10–20 minutes.

When in the lactol of formula (II) B is

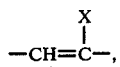

wherein X is chlorine, it is necessary, by using for example 1.5 to 2.5 moles of Wittig reagent per mole of lactol, to prolong the reaction time up to ten hours or, if it is desired to use shorter reaction times, it is necessary to employ a great excess of Wittig reagent (at least 5 moles of Wittig reagent per mole of lactol for reaction times of about 30 minutes).

When in the lactol of formula (II) B is

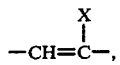

wherein X is bromine, chlorine or iodine, the hydrogen atom linked to the carbon atom in the 13-position and the halogen atom linked to the carbon atom in the 14-position may be either in the trans-position (geometric trans-isomers) or in the cis-position (geometric cis-isomers). Preferably they are in the trans-position.

The Wittig reaction is performed by using the condition generally followed for this kind of reaction, i.e. in an organic solvent, for example diethylether, hexane, dimethylsulphoxide, tetrahydrofuran, dimethylformide or hexamethylphosphoramide, in presence of a base, preferably sodium hydride and potassium tert.butoxide, at 0° C. to the reflux temperature of the reaction mixture, preferably at room temperature or below.

The term "Wittig reagent" includes compounds of general formula

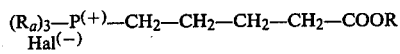

wherein $R_a$ is aryl or alkyl, Hal is bromine or chlorine and R is hydrogen or alkyl. When $R_a$ is alkyl, it is preferably ethyl.

The preparation of the Wittig reagent is discussed in detail by Tripett, Quart. Rev., 1963, XVII, No. 4, 406.

It is evident that for economic reasons, in the lactol of formula (II), B is preferably a

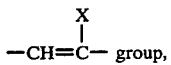

wherein X is preferably bromine or iodine, since both the triple bond formation and the alkylation with the Wittig reagent take place at the same time, in an only one step.

When in the lactol of formula (II) B is

wherein X is bromine, chlorine or iodine, during the reaction with the Wittig reagent, the dehydrohalogenation takes place as easily when the hydrogen atom linked to the carbon atom in the 13-position and the halogen atom linked to the carbon atom in the 14-position are in the trans-position as when they are in the cis-position.

The optional acylation of the 9α-hydroxy group in the compound of formula (III) with a carboxylic acid may be performed e.g. by treatment with an anhydride or with a chloride of a carboxylic acid in presence of a base, i.e. according to the usual methods of organic chemistry.

The deetherification reaction is performed under conditions of mild acid hydrolysis, for example with mono- or polycarboxylic acid, e.g. formic, acetic, oxalic, citric and tartaric acid, and in a solvent, for example water, acetone, tetrahydrofuran, dimethoxyethane and lower aliphatic alcohols.

Preferably, 0.1 N to 0.25 N poly-carboxylic acid (e.g. oxalic or citric acid) is used in presence of a convenient low boiling cosolvent which is miscible with water and which can be easily removed in vacuo at the end of the reaction.

The oxidation of the 9α-hydroxy group to yield an oxo group may be carried out with, for example, Jones reagent.

As above stated, the deetherification of the compound of general formula (IV) may give, according to the reaction conditions used, either a compound of general formula (I) wherein the symbol --- is a single bond, $R_1$ is hydroxy and $R_2$ and $R_3$ taken together form an oxo group, or a compound of general formula (I) wherein the symbol --- is a double bond, $R_1$ is hydrogen and $R_2$ and $R_3$ taken together form an oxo group.

The former compound may be obtained as the only product, by operating at temperatures ranging between about 25° C. and about 35°–38° C., while by operating at higher temperatures, for example at the reflux temperature for about three hours, the latter compound is obtained as the only product.

The lactol of formula (II) may be prepared, in turn, by means of a multi-step process using as starting material an optically active or racemic lactone of formula (V)

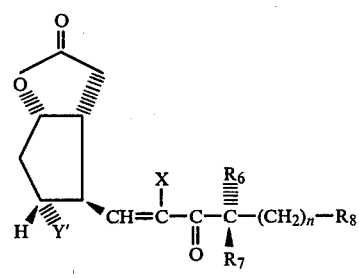

wherein Y' is hydroxy, acyloxy or a known protecting group bound to the ring through an ethereal oxygen atom, X, $R_6$, $R_7$, $R_8$ and n are as defined above; and wherein the hydrogen atom linked to the carbon atom in the 13-position and the halogen atom linked to the carbon atom in the 14-position (prostaglandin numbering) may be either in the trans-position or in the cis-position.

The multi-step process to prepare the compound of general formula (11) starting from the lactone of formula (V) involves the following steps:

(a) reduction of the 15-oxo group (prostaglandin numbering) of the lactone of formula (V) to yield a mixture of 15S- and 15R-ols having the formulae (VIa) and (VIb)

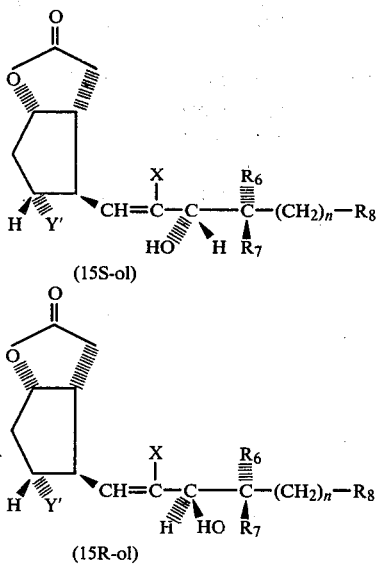

(15S-ol)

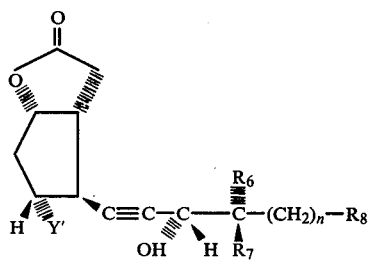

(15R-ol)

wherein Y', X, R$_6$, R$_7$, R$_8$ and n are as above defined, followed by the separation of the 15S-ol from the 15R-ol and, if desired, by the dehydrohalogenation of the separated alcohols to give a compound of formula (VIIa)

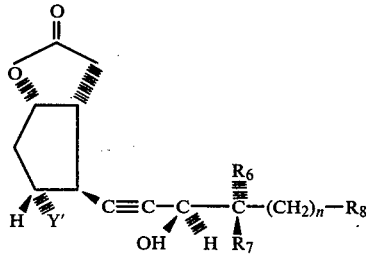

(VIIa)

or a compound of formula (VIIb)

(VIIb)

wherein Y', R$_6$, R$_7$, R$_8$ and n are as above defined. If desired, the reduction may follow the dehydrohalogenation. The reduction of the 15-oxo group may be suitably performed in an organic solvent, such as acetone, diethylether, dimethoxyethane, dioxan, or benzene or their mixtures, by using e.g. metal borohydrides, in particular sodium borohydride, lithium borohydride, zinc borohydride, sodium trimethoxyborohydride.

The separation of the 15S-ol from the 15R-ol may be performed by chromatography, e.g. silica gel chromatography or by fractionated crystallization. The dehydrohalogenation may be performed in a solvent, preferably selected from the group consisting of dimethylsulphoxide, dimethylformamide, hexamethylphosphoramide in presence of a base which may be for example an alkaline metal amide, potassium tert. butylate or the anion

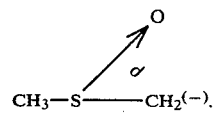

Conversion of a compound of formula (VIII)

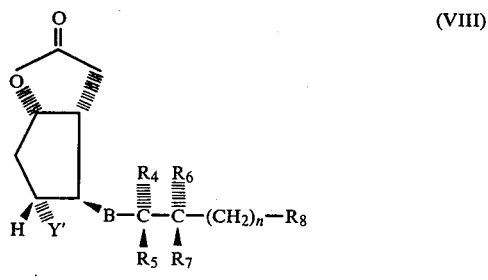

(VIII)

wherein Y', R$_6$, R$_7$, R$_8$, B and n are as defined above and one of R$_4$ and R$_5$ is a hydrogen atom and the other is a hydroxy group into a compound of formula (IX)

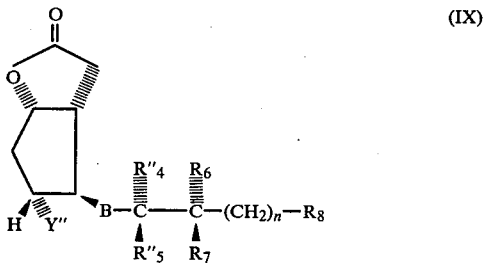

(IX)

wherein B, R$_6$, R$_7$, R$_8$ and n are as defined above, Y'' is a known protecting group bound to the ring through an ethereal oxygen atom, and one of R''$_4$ and R''$_5$ is a known protecting group bound to the chain by an ethereal oxygen atom and the other is a hydrogen atom.

The etherification of the compound of formula (VIII) to give a compound of formula (IX) is preceded when, in the compound of formula (VIII), Y' is an acyloxy group, by saponification for example by mild treatment with an alkali, to give a compound of formula (VIII) wherein Y' is a hydroxy group.

The etherification is preferably carried out with a vinylic ether of formula

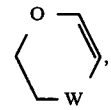

wherein W is —O— or —CH$_2$—, in presence of catalytic amounts of, for example, phosphorus oxychloride, p-toluenesulphonic acid or benzene sulphonic acid, or with a silyl ether, for instance by reacting a trisubstituted chlorosilane in presence of an acceptor base (for example a trialkylamine) of the hydrogen halide formed, or with an enol ether, for instance by reaction, in presence of an acid catalyst with a 1,1-dialkoxycyclopentane or cyclohexane, at the reflux temperature in an inert solvent and distilling the alcohol formed to obtain mixed dialkoxy ethers or enol ethers, according to the quantity of catalyst used or the heating time.

(c) Reduction of the compound of formula (IX) to yield a lactol derivative of formula (X)

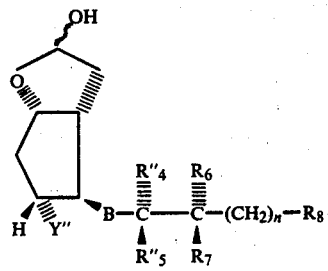

wherein Y''', B, R''$_4$, R''$_5$, R$_6$, R$_7$, R$_8$ and n are as above defined. The reduction may be performed by treatment with diisobutylaluminium hydride or sodium bis-(2-methoxyethoxy)-aluminium hydride in an inert solvent, for example, toluene, n-heptane, n-hexane or benzene or their mixtures, at below 30° C.

(d) Optional deetherification of the compound of formula (X) to give a compound having the free 11- and 15-hydroxy groups. The deetherification may be carried out by mild acid hydrolysis, in a solvent miscible with water, with a solution of a mono- or poly-carboxylic acid.

All the compounds mentioned under items (a) to (d) may be either optically active compounds or racemic mixtures thereof.

The lactone of formula (V) may be in turn prepared in an only one step by reaction of an aldehyde of formula (XI)

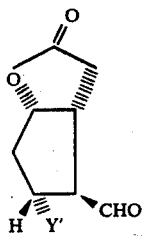

wherein Y' is as defined above with a halo-phosphonate carbanion of formula (XII)

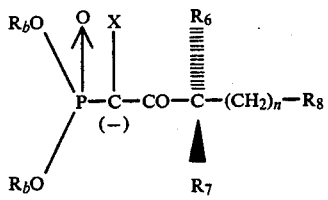

wherein R$_b$ is lower alkyl, X, R$_6$, R$_7$, R$_8$ and n are as defined above.

The reaction is suitably performed in a solvent which is preferably dry benzene, dimethoxyethane, tetrahydrofuran, dimethylformamide or their mixtures, and using a suspension of 1.1–1.2 molar equivalent of the halo-phosphonate carbanion.

When in the aldehyde of formula (XI) Y' is an acyloxy group, it may be for example, acetoxy, propionyloxy, benzoyloxy and p-phenyl-benzoyloxy. When Y' is a known protecting group bound to the ring through an ethereal oxygen atom, it may be for example one of the ethereal protecting groups reported here-above.

The aldehyde of formula (XI) may be prepared substantially as described by E. J. Corey et al., Ann. of New York Acad. of Sciences, 180, 24 (1971).

The halo-phosphonate carbanion of formula (XII) may be in turn prepared by reacting a halo-phosphonate of formula (XIII)

wherein R$_b$, X, R$_6$, R$_7$, R$_8$ and n are as defined above, with an equivalent of a base preferably selected from the group consisting of sodium hydride, lithium hydride, calcium hydride, an alkyl lithium derivative and the anion $CH_3—SO_2—CH_2^{(-)}$.

The halo-phosphonate of formula (XIII) may be obtained by halogenation of a phosphonate of formula (XIV)

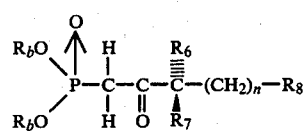

wherein R$_b$, R$_6$, R$_7$, R$_8$ and n are as defined above.

The halogenation may be carried out in a conventional manner, operating substantially as in the halogenation of β-ketoesters. The phosphonate of formula (XIV) may be prepared by known methods, e.g. according to E. J. Corey et al., J. Am. Chem. Soc. 90, 3247 (1968) and E. J. Corey and G. K. Kwiatkowsky, J. Am. Chem. Soc., 88, 5654 (1966). Preferably, the phosphonate of formula (XIV) is prepared by reaction of lithium methylphosphonate with a lower alkylester of the optionally substituted aliphatic acid. When the aliphatic acid contains asymmetric carbon atoms, it is possible to use either the racemic acid or one of its optical antipodes.

The lower alkylester of the suitable aliphatic acid maybe prepared by known methods. For example, the ethyl β-cyclobutylpropionate may be prepared condensing cyclobutyl-formate with a compound of formula

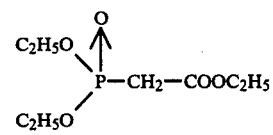

and then reducing, e.g. with Pd/C, the resulting ethyl β-cyclobutylacrylate. The ethyl esters of the γ-cyclopropyl-butyrric, γ-cyclobutyl-butyrric and δ-cyclopropyl-valerianic acids may be prepared, e.g. from the corresponding esters of cyclopropyl-acetic, cyclobutyl-acetic and cyclopropyl-propionic acids, after reduction to the alcohols and conversion into the halides, by malonic synthesis, as is known in organic chemistry, followed by esterification of the obtained acids.

So, in their turn, the esters, e.g. ethyl esters of the substituted propionic acids, [e.g. cyclopropyl, cyclobutyl, cyclopentyl, cycloheptyl, (2'-tetrahydrofuryl), 1-adamantyl, 2-norbornyl, 2-bicyclo[2,2,2]-octyl or 4-t.butyl-cyclohexyl propionic acids], may be prepared starting from the corresponding substituted acetic acids by known methods, e.g. by reduction of the substituted acetic acids to primary alcohols, conversion of the alcohols into the mesylates and then into the halides, and finally by reaction with a cyanide, e.g. an alkaline cyanide, to give the nitriles of the substituted propionic acids which are subsequently converted into the substituted propionic esters by the usual method of organic chemistry. The α-methylation of the enolates of the above-described esters, which can be obtained by reaction of the esters with lithium diisopropylamide in tetrahydrofuran (according to the method described in Org. Synthesis, 50, 58 and in Tetrahedron Letters, 2425 (1973)) gives the α-methyl-substituted esters of the above acids, i.e. for example, α-methyl-β-cyclobutyl-propionic, α-methyl-β-cyclopropylpropionic, α-methyl-β-cyclopentyl-propionic, α-methyl-β-cyclohexyl-propionic, α-methyl-γ-cyclopropyl-butyrric, α-methyl-γ-cyclobutyl-butyrric, α-methyl-δ-cyclopropyl valerianic as well as the α-methyl-substituted esters of the other above-cited acids, which may be optionally resolved into the optical antipodes to give the 2S-methyl and the 2R-methyl derivative. The further methylation of the above-cited esters gives the α,α-dimethyl substituted esters of the above acids, i.e., for example, α,α-dimethyl-β-cyclobutyl propionic, α,α-dimethyl-β-cyclopropyl-propionic, α,α-dimethyl-β-cyclopentyl-propionic, α,α-dimethyl-β-cyclohexyl-propionic, α,α-dimethyl-γ-cyclopropyl-butyrric, α,α-dimethyl-γ-cyclobutyl-butyrric, α,α-dimethyl-δ-cyclopropyl valerianic as well as the α,α-dimethyl-substituted-esters of the above-cited acids.

Alternatively, the halo-phosphonate carbanion of formula (XII) may be prepared by reacting a phosphonate carbanion of formula (XIVa)

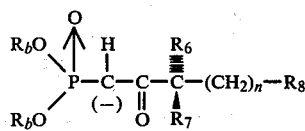

wherein $R_b$, $R_6$, $R_7$, $R_8$ and n are as defined above, with a halogenating agent selected from the group consisting of $Br_2$, pyrrolidone-hydrotribromide (PHTB), dioxandibromide, N-chloroacetamide, N-chlorosuccinimide, N-bromosuccinimide, N-bromoacetamide, N-bromocaprolactame, N-iodosuccinimide.

By using the imides as halogenating agents, the carbanion of the halo-phosphonate of formula (XII) is obtained directly with the use of only one equivalent of base; otherwise, it should be necessary to use another equivalent of a base to obtain the carbanion of the halo-phosphonate.

The phosphonate carbanion of formula (XIVa) may be in turn obtained by the treatment of the phosphonate of formula (XIV) with an equivalent of a base, e.g. sodium, lithium or calcium hydride.

The halo-lactone of formula (V) wherein X is bromine may also be obtained by a multi-step process starting from a lactone of formula (XV)

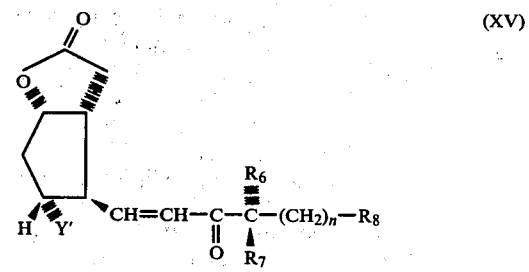

wherein Y', $R_6$, $R_7$, $R_8$ and n are as defined above, which may be prepared substantially as described by E. J. Corey et al., Annals of New York Acad. of Sciences, 180, 24 (1971). This multi-step process involves the following steps:

(a') reduction of the lactone of formula (XV) to give a mixture of the 15S- and 15R-ols of formulae (XVIa) and (XVIb)

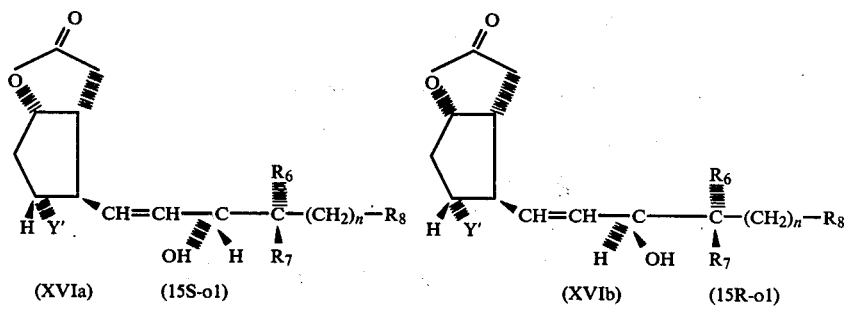

wherein Y', $R_6$, $R_7$, $R_8$ and n are as defined above.

The reduction may be performed in an organic solvent, such as acetone, diethylether and dimethoxyethane, by using, for example, sodium borohydride, zinc borohydride, and lithium borohydride.

(b') halogenation of the mixture of the two 15R- and 15S-ols to give a mixture of 13ξ,14ξ-dibromoalcohols of formulae (XVIIa) and (XVIIb)

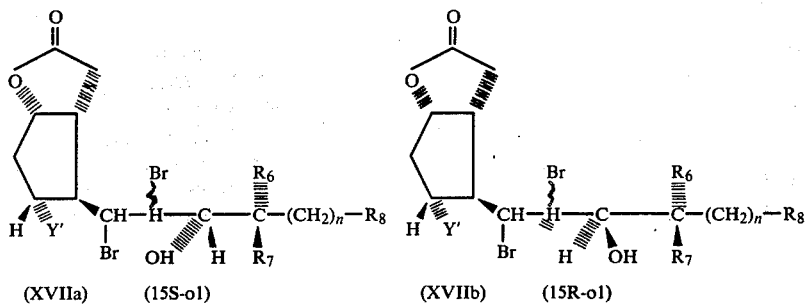

wherein Y', $R_6$, $R_7$, $R_8$ and n are as defined above.

The halogenation is carried out in a inert solvent, preferably selected from the group consisting of a halogenated solvent, e.g. dichloromethane, dichloroethane, $CCl_4$ and a linear or cyclic ether, e.g. tetrahydrofuran, dioxane, dimethoxyethane or their mixtures, using the molar equivalent of halogenating agent or an excess of the same agent, which may be, e.g. $Br_2$, dioxandibromide, pyrrolidone hydrotribromide.

(c') oxidation of the mixture of the 13ξ,14ξ-dibromoalcohols to give a 13ξ,14ξ-dibromo-15-oxo-derivative of formula (XVIII)

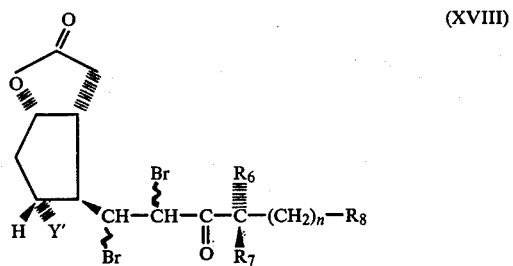

(XVIII)

wherein Y', $R_6$, $R_7$, $R_8$ and n are as defined above.

The oxidation is carried out at a temperature ranging between $-25°$ and the room temperature, by using a dichloromethane solution of the pyridine-chromic anhydride complex or a sulphoric solution of chromic anhydride in acetone (Jones reagent), or a carbodiimide, working in dimethylsulphoxide in presence of a suitable acid.

(d') dehydrohalogenation of the 13ξ14ξ-dibromo-15-oxo-derivative to give the halo-lactone of formula (V) wherein X is bromine.

The dehydrohalogenation may be performed by using an organic base, for example a tert.amine in an inert solvent, or alternatively by using an inorganic base, for example potassium acetate in a solvent such as methanol, ethanol and the like.

A further alternative process for the preparation of the halo lactone of formula (V) wherein X is bromine is the reaction of the lactone of formula (XV), in an ethereal anhydrous solvent such as tetrahydrofuran and dimethoxyethane with a halogenating agent such as phenyltrimethylammoniumtribromide and in particular pyrrolidione-hydrotribromide (1.1–1.3 molar equivalents) to give directly the 13ξ,14ξ-dibromo-15-oxo-derivative of formula (XVIII) which is then dehydrohalogenated as above described, to give the halo-lactone of formula (V), wherein X is bromine.

Also in the alternative methods for the preparation of the halo-lactone of formula (V), all the compounds may be either optically active compounds or racemic mixtures thereof.

In the preparation of the halo-lactone of formula (V) according to the here-above described methods, both compounds wherein the hydrogen atom linked to the carbon atom in the 13-position and the halogen atom linked to the carbon atom in the 14-position (prostaglandin numbering) are in the trans-position (geometric trans-isomers) and compounds wherein said atoms are in the cis-position (geometric cis-isomers) are obtained.

The geometric trans-isomers are obtained in a far higher percentage (92–95%), while the geometric cis-isomers are obtained in a far lower percentage (5–8%).

The geometric trans-isomers of formula

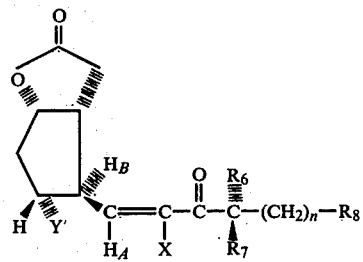

can be easily distinguished from the geometric cis-isomers of formula

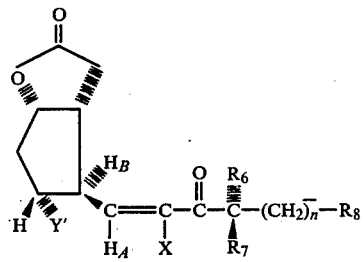

in that the $H_A$ vinylic protons of the two isomers resonate at different positions and the coupling constants of the $H_A$ vinylic proton with the $H_B$ proton are well different (respectively 9 Hz for the trans-isomer and 10.2 Hz for the cis-isomer).

Anyway, both the trans-isomers and the cis-isomers are intermediates for the synthesis of the 13,14-dehydro-prostaglandins of the invention.

The lactol of formula (II) wherein B is —C≡C— may be also prepared by dehydrohalogenation of the lactol of formula (II) wherein B is

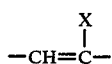

wherein X is bromine, chlorine or iodine. The dehydrohalogenation may be carried out in an aprotic solvent preferably selected from the group consisting of dimethylsulphoxide, dimethylformamide and hexamethylphosphoramide by treatment with a base preferably selected from the group consisting of potassium tert.butylate, an alkali metal amide and the anion $CH_3—SO—CH_2^{(-)}$.

Among the intermediates described in this specification, the following are compounds of the invention:
(1) the halo-phosphonate carbanion of formula (XII);
(2) the lactol of formula (II);
(3) the lactone of formula (XIX)

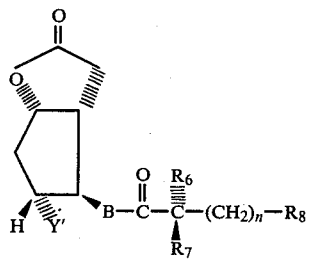

wherein Y′, B, $R_6$, $R_7$, $R_8$ and n are as defined above;
(4) a compound of formula (XX)

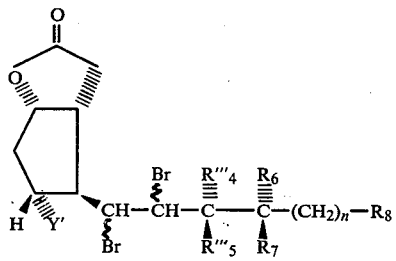

wherein Y′, $R_6$, $R_7$, $R_8$ and n are as defined above, and one of $R_4'''$ and $R_5'''$ is hydroxy and the other is hydrogen, or $R_4'''$ and and $R_5'''$ together form an oxo group;
(5) a compound of formula (XXI)

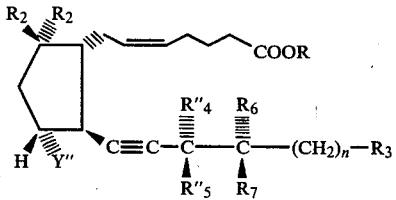

wherein R is hydrogen or $C_1$- $C_{12}$ alkyl, Y″, $R_4''$, $R_5''$, $R_6$, $R_7$, $R_8$ and n are as defined above, $R_2$ is hydrogen and $R_3$ is hydroxy or a carboxylic acyloxy or $R_2$ or $R_3$ together form an oxo group.

All the intermediates mentioned under the foregoing points (1) to (5) are optionally active or racemic compounds.

The compounds of formula (I) may be used for the same therapeutical indications as natural prostaglandins, with respect to which, however, they offer the advantage of being no substrates for the enzyme 15-prostaglandin dehydrogenase, which as is known, quickly inactivates natural prostaglandins, and, furthermore, are characterized by a more selective therapeutical action.

The compounds of formula (I) furthermore inhibit the use of natural prostaglandins as substrate by the enzyme. Using the 15-hydroxy-prostaglandin-dehydrogenase drawn from human placenta, in vitro tests carried out with for example 13,14-dehydro-17-cyclohexyl-20,19,18-trinor-$PGF_{2\alpha}$(5c-9α,11α,15S-trihydroxy-20,19,18-trinor-17-cyclohexyl-prost-5-en-13-ynoic acid), showed that, while the inhibition with respect to $PGE_2$ is of a non-competitive kind ($K_i=468$ μM), the inhibition becomes partially competitive with respect to $PGF_{2\alpha}$ ($K_i=152$ μM).

The same compound (13,14-dehydro-17-cyclohexyl-20,19,18-trinor-$PGF_{2\alpha}$) was compared with $PGF_{2\alpha}$ and with the olefinic analogue 5c,13t-9α,11α,15S-trihydroxy-20,19,18-trinor-17-cyclohexyl-prosta-5,13-dienoic acid (17-cyclohexyl-20,19,18-trinor-$PGF_{2\alpha}$) in the following in vitro tests: guinea pig ileum test, rat uterus test, rat stomach fundus. The results are reported in the following Table, wherein to the activity of $PGF_2$ the conventional value of 1 was given in all the tests. The three tests relate to the determination of the spasmogenic activity.

| Compound | Guinea Pig Ileum | Rat Uterus | Rat Stomach Fundus |
|---|---|---|---|
| $PGF_{2\alpha}$ | 1 | 1 | 1 |
| 17-cyclohexyl-20,19,18--trinor-$PGF_{2\alpha}$ | 0.60 | 3.23 | 1.86 |
| 13,14-dehydro-17-cyclo=hexyl-20,19,18-trinor--$PGF_{2\alpha}$ | 0.17 | 15.7 | 1.96 |

The guinea pig ileum test consisted of a 10 ml thermostatic bath held at 35° C., containing the ileum of a male guinea pig, under 0.5 g traction, carboxygenated in a Tyrode solution; this was left for 30 minutes to stabilize before the compounds were tested. The response was recorded using a isotonic frontal lever, long enough to amplify the response 4.5 times.

The rat uterus test consisted of a 10 ml thermostatic bath held at 29° C., in which oestrogenized rat uteri under 0.5 g traction were carboxygenated in a Dejalon saline solution. The preparation was left to stabilize for 30 minutes before the compounds were tested. Response was measured using a isotonic frontal lever, long enough to amplify the response 4.5 times.

The rat stomach fundus test was performed in the following manner: male albino rats of the Sprague-Dawley strain weighing 200–250 g were utilized. The stomach fundus strip was prepared according to Vane (J. R. Vane, Brit. J. Pharmacol, 12, 344, (1957)). The strip was suspended in a 10 ml organ bath containing Tyrode solution gassed with a mixture of $O_2$ and $CO_2$ (95:5%). The contractions of the strip were recorded using a isotonic frontal lever as in the preceding tests.

From the comparison of the activities in the three in vitro tests, it results evident that, independently from the species of animals used, a remarkable increase of the action selectivity on miometrium was obtained as well as a reduced effect on the muscle of the gastroenteric apparatus was recorded, that means, a reduction of the gastrointestinal side-effects which are always present when natural prostaglandins are administered. In fact, the comparison of the ratios uterus/ileum and uterus/stomach fundus shows that said ratios are much more favourable when the 13,14-dehydro analogues are employed:

| Compound | Uterus/Ileum | Uterus/Stomach Fundus |
| --- | --- | --- |
| $PGF_{2\alpha}$ | 1 | 1 |
| 17-cyclohexyl-20,19,18-trinor-$PGF_{2\alpha}$ | 5.4 | 1.7 |
| 13,14-dehydro-17-cyclohexyl-20,19,18-trinor-$PGF_{2\alpha}$ | 91 | 8 |

The action selectivity of the 13,14-dehydro compounds on the miometrium and on the reproductive apparatus is also proven by the remarkable increase of the luteolytic activity in the pregnant rat at the 9th–10th day of pregnancy. In fact, if the conventional value of 1 is given to the luteolytic activity of $PGF_{2\alpha}$, the value of 30 is to be given to the luteolytic activity of 17-cyclohexyl-20,19,18-trinor-$PGF_{2\alpha}$, and the value of 200 to the luteolytic activity of 13,14-dehydro-17-cyclohexyl-20,19,18-trinor-$PGF_{2\alpha}$.

Besides, the compounds of formula (I), e.g. 13,14-dehydro-17-cyclohexyl-20,19,18-trinor-$PGF_{2\alpha}$, when tested against $PGF_{2\alpha}$ on the rat uterus, are able to antagonize $PGF_{2\alpha}$ specifically and selectively.

The 9-oxo-derivatives (PGE analogues) of formula (I) when compared with $PGE_2$ according to the method described by H. Shay et al., Gastroenter., 26, 906 (1954) are 2 to 4 times more active as gastric antisecretory agents than $PGE_2$.

Moreover, the antisecretory activity of the 9-oxo-compounds of formula (I), wherein one lower alkyl, particularly a methyl, is present on the carbon atom in the 16-position, is further increased of 2 times when the alkyl is a 16S- alkyl, and of 4 times when the alkyl is a 16R- alkyl.

The compounds of formula (I) can be administered orally, parenterally, or by intravenous or intrauterine (extra-amniotic or intra-amniotic) way, by rectal suppositories or by inhalation. For example, they can be administered by intravenous infusion of a sterile isotonic saline solution at the rate of 0.01 to 10, preferably 0.05 to 1, μg/kg of mammal body weight per minute.

The invention therefore also provides a pharmaceutical composition comprising a compound of general formula (I) and a pharmaceutically acceptable carrier or diluent.

The compositions may be prepared by conventional methods and can be, for example, in the form of tablets, capsules, pills, suppositories or bougies, or in liquid form e.g. solutions, suspensions or emulsions.

Examples of substances which can serve as carriers or diluents are water, gelatin, lactose, starches, magnesium stearate, talc, vegetable oil, benzyl alcohol and cholesterol.

The invention is illustrated by the following examples, wherein the abbreviations "THP", "DIOX", "DMSO", "THF", "DMF", "DIBA", and "Et₂O" refer to tetrahydropyranyl, dioxanyl, dimethylsulphoxide, tetrahydrofuran, dimethylformamide, diisobutylaluminium hydride and ethyl ether, respectively.

EXAMPLE 1

Under a nitrogen atmosphere, a suspension of 80% NaH (dispersion in mineral oil) (0.48 g) in dry DMSO (12 ml) was heated with stirring at 60° until no more hydrogen evolved (about 3 hours). The stirred mixture of methylsulphinyl carbanide, $CH_3SOCH_2^{(-)}$, was cooled at 5–8° (and treated with crystalline triphenyl-(4-carboxybutyl)-phosphoniumbromide (3.42 g) and the stirring was continued until this compound was completely dissolved. The deep orange-red solution of the ylide: $(C_6H_5)_3-P-CH^{(-)}-(CH_2)_3-CO_2^{(-)}$ was then treated with a solution of 5β-(2'-bromo-3'S-hydroxy-5'-cyclohexyl-pent-1'-trans-1'-enyl)-2α,4α-dihydroxy-cyclopentan-1α-ethanal-γ-lactol-3',4'-bis-THP-ether (0.6 g) in dry DMSO (8 ml). After stirring overnight, under nitrogen atmosphere at room temperature, the reaction mixture was diluted with water (20 ml) and the alkaline phase was repeatedly extracted with ether to remove the triphenylphosphoxide; the ethereal extracts were combined, back-washed with 0.5 N NaOH and then discarded. The alkaline washes were combined with the original alkaline phase, acidified to pH 4.8 and extracted several times with ethyl ether-pentane 1:1. The combined organic extracts were washed with saturated $(NH_4)_2SO_4$ solution, dried on $Na_2SO_4$ and evaporated to dryness, yielding 0.55 g of 5c-9α,11α,15S-trihydroxy-18,19,20-trinor-17-cyclohexyl-prost-5-en-13-ynoic acid-11,15-bis-THP-ether (ω-trinor-17-cyclohexyl-13,14-dehydro-$PGF_{2\alpha}$-11,15-bis-THP-ether), an oil with $[\alpha]_D = -7.8°$. Under the same conditions, starting with the 15-epimeric lactol: 5β-(2'-bromo-3'R-hydroxy-5'-cyclohexyl-pent-1'-trans-1'-enyl)-2α,4α-dihydroxy-cyclopentan-1α-ethanal-γ-lactol-3',4'-bis-THP-ether, the product obtained was 5c-9α,11α,15R-trihydroxy-18,19,20-trinor-17-cyclohexyl-prost-5-en-13-ynoic acid-11,15-bis-THP-ether (ω-trinor-17-cyclohexyl-13,14-dehydro-15-epi-$PGF_{2\alpha}$-bis-THP-ether).

Individually, 250 mg of each of the two compounds was dissolved in 12 ml of acetone and refluxed with 0.2 N oxalic acid (10 ml) three hours.

The acetone was evaporated off and the aqueous phases were extracted with ethyl acetate. The organic extracts for each product were combined, dried on $Na_2SO_4$ and the ethyl acetate removed by vacuum.

The resulting crude products were chromatographed on acid-washed silica gel (12 g) eluted with methylene chloride containing 15% ethyl acetate and then 20% ethyl acetate, to yield respectively 151 mg of 5c-9α,11α,15S-trihydroxy-18,19,20-trinor-17-cyclohexyl-prost-5-en-13-ynoic acid (ω-trinor-17-cyclohexyl-13,14-dehydro-$PGF_{2\alpha}$), $[\alpha]_D = +24°$, $[\alpha]_{365°} = +78°$ (EtOH), and 142 mg of 5c-9α,11α,15R-trihydroxy-18,19,20-trinor-17-cyclohexyl-prost-5-en-13-ynoic acid (ω-trinor-17-cyclohexyl-13,14-dehydro-15-epi-$PGF_{2\alpha}$), $[\alpha]_D = +17.8°$ (EtOH).

EXAMPLE 2

Working in dry box and under nitrogen atmosphere, at 5°–10° C., a solution of triphenyl-(4-carboxy-butyl)-phosphonium bromide (2.66 g) in 5 ml of dry DMSO, was added with stirring to a suspension in DMSO of the carbanion $CH_3SOCH_2^{(-)}$, obtained by heating at 60° for 3 hours a suspension of 0.365 g of 80% NaH in 10 ml of dry DMSO. To the dark red solution of the ylide was then added 5 ml of a DMSO solution of 425 mg of 5β-(2'-chloro-3'S-hydroxy-4'(S,R)-methyl-5'-cyclohexyl-pent-1'-trans-1'-enyl)-2α,4α-dihydroxy-cyclopentane-1α-ethanal-γ-lactol-3',4-bis-DIOX-ether. The reaction mixture was stirred for 12 hours at room temperature. After dilution with water it was extracted with ethyl ether to remove the triphenylphosphoxide. The ether extracts were back-washed with diluted alkali (0.5 N NaOH) and then discarded. The combined aqueous alkaline fractions were acidified to pH 4.8 with 2 N sulfuric acid and extracted with a 1:1 mixture of pentane: ethyl ether.

These extracts were washed until neutral and the solvent evaporated to yield 0.428 g of 5c-9α,11α,15S-trihydroxy-18,19,20-trinor-17-cyclohexyl-16(S,R)-methyl-prost-5-en-13-ynoic acid-11,15-bis-DIOX-ether. 0.128 g of this product were deacetalated by the method described in Example 1, yielding, after chromatography on acid-washed silica gel eluted with $CH_2Cl_2$-ethyl acetate 70:30, 62 mg of 5c-9α,11α,15S-trihydroxy-18,19,20-trinor-17-cyclohexyl-16(S,R)-methyl-prost-5-en-13-ynoic acid, or ω-trinor-17-cyclohexyl-16(S,R)-methyl-13,14-dehydro-PGF$_{2α}$, $[α]_D = +13°$ (EtOH).

EXAMPLE 3

Under inert gas atmosphere, to a solution of cooled (about 12°-14° C.) triphenyl-(4-carboxy-butyl)-phosphonium bromide (3.1 g) in DMSO was added a solution of potassium tert.-butoxide (1.58 g). The stirring was continued until a strongly colored solution of the ylide was obtained, then 0.573 g of 5β-(2'-bromo-3'S-hydroxy-4'S-methyl-5'-cyclohexyl-pent-1'-trans-1'-enyl)-2α,4α-dihydroxy-cyclopentane-1α-ethanal-γ-lactol-3'S,4-bis-THP-ether, dissolved in a minimum quantity of dry DMSO, was added. The reaction mixture was stirred for 3 hours at room temperature, then placed in an ice bath and diluted with an equal volume of water. The alkaline aqueous phase was extracted with ethyl ether to remove the $(C_6H_5)_3P=O$. The ether extracts were back-washed with N NaOH and then discarded.

The aqueous alkaline phases were combined, acidified to pH 5 and extracted with ethyl ether-pentane 1:1, to give 0.52 g of 5c-9α,11α,15S-trihydroxy-18,19,20-trinor-17-cyclohexyl-16S-methyl-prost-5-en-13-ynoic acid-11,15-bis-THP-ether.

A solution of 0.25 g of this compound in 6 ml of tetrahydrofuran was refluxed for 3 hours with 5 ml of 0.2 N oxalic acid. The THF was removed by vacuum and the residue extracted with ethyl acetate. The combined ethyl acetate extracts were washed until neutral with a saturated $(NH_4)_2SO_4$ solution, dried and the solvent removed by evaporation. The residue was chromatographed on silicic acid gel (9 g) eluted with $CH_2Cl_2$ and with $CH_2Cl_2$-ethyl acetate 75:25, giving 120 mg of 5c-9α,11α,15S-trihydroxy-18,19,20-trinor-17-cyclohexyl-16S-methyl-prost-5-en-13-ynoic acid (ω-trinor-16S-methyl-17-cyclohexyl-13,14-dehydro-PGF$_{2α}$), $[α]_D = +14°$ (EtOH).

EXAMPLE 4

Using one of the procedures described in Examples 2 and 3, by reacting a DMSO solution of the ylide of triphenyl-(4-carboxy-butyl)-phosphonium bromide (6 moles) with one mole of a 3',4-bis-acetalic-ether (dioxanylether or tetrahydropyranylether) of a γ-lactol chosen from the group of 2α,4α-dihydroxy-cyclopentane-1α-ethanal-γ-lactol:

5β-(2'-bromo-3'S-hydroxy-4'S-methyl-5'-cyclohexyl-pent-1'-trans-1'-enyl);

5β-(2'-bromo-3'S-hydroxy-4'R-methyl-5'-cyclohexyl-pent-1'-trans-1'-enyl);

5β-(2'-bromo-3'R-hydroxy-4'S-methyl-5'-cyclohexyl-pent-1'-trans-1'-enyl);

5β-(2'-bromo-3'R-hydroxy-4'R-methyl-5'-cyclohexyl-pent-1'-trans-1'-enyl);

the 11,15-bis-acetalic ethers (11,15-bis-DIOX-ethers and 11,15-bis-THP-ethers) of the corresponding prost-5-en-13-ynoic acids are obtained, which are then deacetalated to give, respectively:

5c-9α,11α,15S-trihydroxy-18,19,20-trinor-17-cyclohexyl-16S-methyl-prost-5-en-13-ynoic acid, $[α]_D = +14°$ (CHCl$_3$);

5c-9α,11α,15S-trihydroxy-18,19,20-trinor-17-cyclohexyl-16R-methyl-prost-5-en-13-ynoic acid, $[α]_D = +16°$ (CHCl$_3$);

5c-9α,11α,15R-trihydroxy-18,19,20-trinor-17-cyclohexyl-16S-methyl-prost-5-en-13-ynoic acid, $[α]_D = +12°$ (CHCl$_3$);

5c-9α,15R-trihydroxy-18,19,20-trinor-17-cyclohexyl-16R-methyl-prost-5-en-13-ynoic acid, $[α]_D = +11°$ (CHCl$_3$).

EXAMPLE 5

To a stirred solution of the ylide obtained by treatment of a solution of triphenyl-(4-carboxybutyl)-phosphonium bromide (2.4 g) in dry DMSO (8 ml) with 1.23 g of potassium-tert.-butoxide, cooled to 5°-8°, under inert gas, 0.42 g of 5β-(2'-bromo-3'S-hydroxy-5'-(2'-norbornyl)-pent-1'-trans-1'-enyl)-2α,4α-dihydroxy-cyclopentane-1α-ethanal-γ-lactol-3',4-bis-DIOX-ether were added. After stirring for 8 hours at room temperature, the mixture was diluted with water (13 ml) and after extraction of the alkaline solution with ethyl ether to remove the triphenylphosphoxide, back-washing of the ether extracts with 0.5 N NaOH, and discarding of the ether phase, the combined aqueous phases were acidified to pH 4.6. The following extraction with ethyl ether-pentane 1:1 yielded 0.39 g of 5c-9α,11α,15S-trihydroxy-18,19,20-trinor-17-(2'-nor-bornyl)-prost-5-en-13-ynoic acid-11,15S-bis-DIOX-ether. One hundred mg of this compound were deacetalated in acetone-0.2 N oxalic acid, to give 48 mg of ω-trinor-17-(2'-nor-bornyl)-13,14-dehydro-PGF$_{2α}$.

EXAMPLE 6

In dry conditions under inert gas atmosphere a suspension of 0.48 g of 80% sodium hydride in 12 ml of DMSO was heated for 3 hours at 60° C., until all the hydrogen had evolved, giving a solution of $CH_3SOCH_2^{(-)}$ in DMSO. This was cooled to 0°-5° and 3.5 g of triphenyl-(4-carboxy-butyl)-phosphonium bromide were added and stirred until a deep red solution of the ylide was obtained. To this was then added 0.37 g of 5β-(2'-bromo-3'S-hydroxy-5'-(2'-tetrahydrofuryl)-pent-1'-trans-1'-enyl)-2α,4α-dihydroxy-cyclopentane-1α-ethanal-γ-lactol dissolved in a ml of dry DMSO. This was stirred for 4 hours at room temperature, then diluted with water. It was extracted repeatedly with ethyl ether to remove the triphenylphosphoxide. The combined ether extracts were back-washed with alkali and then discarded. The aqueous alkaline phases were combined, acidified to pH 4.6 with sulfuric acid and extracted with ethyl acetatepentane 1:1. These organic extracts were combined, washed until neutral with ammonium sulfate, dried and evaporated to dryness.

The residue was chromatographed on silicic acid gel (15 g), eluted with methylene chloride-ethyl acetate, to give 0.26 g of 5c-9α,11α,15S-trihydroxy-18,19,20-trinor-17-(2'-tetrahydrofuryl)-prost-5-en-13-ynoic acid (ω-trinor-17-(2'-tetrahydrofuryl)-13,14-dehydro-PGF$_{2α}$).

Using the same procedure, but replacing the lactol derivative with 5β-(2'-bromo-3'S-hydroxy-5'-(2'-tetrahydrofuryl)-pent-1'-trans-1'-enyl)-2α,4α-dihydroxy-cyclopentane-1α-acetic acid-γ-lactol, gave the ω-trinor-17-(2'-tetrahydrothiophenyl)-13,14-dehydro-PGF$_{2α}$.

EXAMPLE 7

Using the procedure described in Example 1, 0.3 g of NaH (80% dispersion in mineral oil) in 9 ml of DMSO was reacted to make the carbanion CH$_3$SOCH$_2^{(-)}$, and then treated with 2.2 g of triphenyl-(4-carboxy-butyl)-phosphonium bromide to give the ylide.

The solution of the ylide was cooled to 10°–12° C., and under argon, 520 mg of 5β-(2'-bromo-3'S-hydroxy-5-(2'-bicyclo[2,2,2]octyl)-pent-1'-trans-1'-enyl)-2α,4α-dihydroxycyclopentane-1α-ethanal-γ-lactol-3',4-bis-DIOX-ether were added. This was stirred for 2 hours and then diluted with 15 ml of water. It was extracted with benzene-ethyl ether 7:3 to remove the triphenylphosphoxide. The organic extracts were back-washed with 0.6 N NaOH and discarded. The alkaline aqueous phases were combined and acidified to pH 4.6 and then extracted with ether:pentane 1:1. The combined organic extracts were washed to neutral with a saturated solution of ammonium sulfate, dried and evaporated to dryness. 0.48 g of 5c-9α,11α,15S-trihydroxy-18,19,20-trinor-17-(2'-bicyclo[2,2,2]octyl)-prost-5-en-13-ynoic acid-11,15-bis-DIOX-ether was obtained.

0.25 g of this compound were refluxed with 10 ml of acetone and 8 ml of 0.2 N citric acid. The acetone was removed in vacuo and the residue extracted with ethyl acetate. The combined ethyl acetate extracts were washed until neutral, dried on Na$_2$SO$_4$ and evaporated to dryness. The residue was chromatographed on silicic acid gel and eluted with cyclohexane-ethyl acetate to give 0.11 g of ω-trinor-17-(2'-bicyclo[2,2,2]octyl)-13,14-dehydro-PGF$_{2α}$.

In a similar way, starting with one of the 3',4-bis-acetalic ethers of the γ-lactols listed below:

5β-(2'-bromo-3'S-hydroxy-5'-cycloheptyl-pent-1'-trans-1'-enyl)-2α,4α-dihydroxy-cyclopentane-1α-ethanal-γ-lactol;

5β-(2'-bromo-3'S-hydroxy-5'-(1'-adamantyl)-pent-1'-trans-1'-enyl);

5β-(2'-bromo-3'S-hydroxy-5'-(4"-tert-butyl-cyclohexyl)-pent-1'-trans-1'-enyl);

5β-(2'-bromo-3'S-hydroxy-6'-cyclohexyl-hex-1'-trans-1'-enyl);

5β-(2'-bromo-3'S-hydroxy-4'-cyclohexyl-but-1'-trans-1'-enyl);

5β-(2'-bromo-3'S-hydroxy-4'-cyclopentyl-but-1'-trans-1'-enyl);

5β-(2'-bromo-3'S-hydroxy-5'-cyclopropyl-pent-1'-trans-1'-enyl);

5β-(2'-bromo-3'S-hydroxy-5'-cyclopentyl-pent-1"-trans-1'-enyl);

5β-(2'-bromo-3'S-hydroxy-4'R-methyl-5'-cyclopentyl-pent-1'-trans-1'-enyl);

5β-(2'-bromo-3'S-hydroxy-4'-(1"'-adamantyl)-but-1'-trans-1'-enyl);

the 11,15-bis acetalic ethers (11,15-bis-DIOX-ethers and 11,15-bis-THP-ethers) of the corresponding prost-13-ynoic acids were obtained, which were then deacetalated to give the following free acids:

5c-9α,11α,15S-trihydroxy-18,19,20-trinor-17-cycloheptyl-prost-5-en-13-ynoic acid, [α]$_D$= +22° (EtOH);

5c-9α,11α,15S-trihydroxy-18,19,20-trinor-17-(1'-adamantyl)-prost-5-en-13-ynoic acid;

5c-9α,11α,15S-trihydroxy-18,19,20-trinor-17-[(4'-tert-butyl)-cyclohexyl]-prost-5-en-13-ynoic acid;

5c-9α,11α,15S-trihydroxy-19,20-dinor-18-cyclohexyl-prost-5-en-13-ynoic acid, [α]$_D$= +18°; [α]$_{365°}$= +44° (EtOH);

5c-9α,11α,15S-trihydroxy-17,18,19,20-tetranor-16-cyclohexyl-prost-5-en-13-ynoic acid [α]$_D$= +18°, [α]$_{365°}$= +38° (EtOH);

5c-9α,11α,15S-trihydroxy-17,18,19,20-tetranor-16-cyclopentyl-prost-5-en-13-ynoic acid [α]$_D$= +19° (EtOH);

5c-9α,11α,15S-trihydroxy-18,19,20-trinor-17-cyclopropyl-prost-5-en-13-ynoic acid, [α]$_D$= +21° (EtOH);

5c-9α,11α,15S-trihydroxy-18,19,20-trinor-17-cyclopentyl-prost-5-en-13-ynoic acid, [α]$_D$= +20° (EtOH);

5c-9α,11α,15S-trihydroxy-18,19,20-trinor-17-cyclopentyl-16R-methyl-prost-5-en-13-ynoic acid;

5c-9α,11α,15S-trihydroxy-17,18,19,20-tetranor-16-(1'-adamantyl)-prost-5-en-13-ynoic acid.

EXAMPLE 8

A solution of 0.395 g of 5β-(2'-chloro-3'S-hydroxy-4'S-methyl-5'-cyclopentyl-pent-1'-trans-1'-enyl)-2α,4α-dihydroxy-cyclopentane-1α-ethanal-ε-lactol-3',4-bis-THP-ether in 4 ml of DMSO was reacted with a solution of the ylide obtained by the procedure outlined in Example 1, starting with 0.34 g of NaH (80% dispersion in mineral oil), 9 ml of DMSO and 2.4 g of triphenyl-(4-carboxybutyl)-phosphonium bromide. The reaction mixture was allowed to stand for 8 hours at room temperature and for 2 hours at 38° C.

It was then cooled and diluted with 13 ml of water, and extracted with benzene-ethyl ether 70:30 to remove the triphenylphosphoxide. The organic extract was back-washed with O.SN NaOH and discarded. The aqueous alkaline fractions were combined, acidified to pH 4.6 and extracted with ether-pentane to give 0.34 g of 5c-9α,11α,15S-trihydroxy-18,19,20-trinor-cyclopentyl-16S-methyl-prost-5-en-13-ynoic acid-11,15-bis-THP-ether.

When 0.17 g of this compound were deacetalated in THF-0.2 N oxalic acid, 98 mg of ω-trinor-17-cyclopentyl-16S-methyl-13,14-dehydro-PGF$_{2α}$, [α]$_D$= +16° (EtOH), were obtained,

EXAMPLE 9

A solution of 0.34 g of 5β-(2'-bromo-3'S-hydroxy-5'-cyclohexyl-pent-1'-trans-1'-enyl)-cyclopentane-2α,4α-dihydroxy-1α-ethanal-γ-lactol in 5 ml of trimethylorthoformate and 25 ml of benzene was heated with 1.9 g of p-toluensulfonic acid for 2 hours at 40° C. Then 30 mg of anhydrous potassium carbonate were added and stirred for 10 minutes, after which the material was transferred to a separatory funnel, washed with 8% NaHCO$_3$ and with water until neutral, dried and evaporated to dryness.

The residue of 5β-(2'-bromo-3'S-hydroxy-5'-cyclohexyl-pent-1'-trans-1'-enyl)-cyclopentane-2α,4α-dihydroxy-1α-ethanal-γ-lactol methyl ether was thoroughly dried and dissolved in 3 ml of DMSO. This solution was added to a solution of 150 mg of potassium tert-butoxide in DMSO. After 3 hours at room temperature, it was diluted with water and extracted with ethyl ether to obtain 0.24 g of 5β-(3'-hydroxy-5-cyclohexylpent-1'-ynyl)-cyclopentane-2α,4α-dihydroxy-1α-ethanal-γ-lactol-methyl ether which was deacetalated with acetone and 0.2 N oxalic acid (10 ml–8 ml for 2 hours, reflux) to give 0.24 g of 5β-(3'S-hydroxy-5-cyclohexyl-pent-1'-ynyl)-cyclopentane-2α,4α-dihydroxy-1α-ethanal-γ-lactol.

A solution of this compound in DMSO was combined with a solution of the ylide of triphenyl-(4-carboxybutyl)-phosphonium bromide prepared from NaH (80% dispersion in mineral oil, 150 mg), 5 ml of DMSO and 1.1 g of triphenyl-(4-carboxybutyl)-phosphonium bromide.

The reaction mixture was stirred for 45 minutes, then diluted with water. The triphenylphosphoxide was extracted with ethyl ether which was back-washed with 0.8 N NaOH. The combined alkaline phases were acidified with 2 N sulfuric acid to pH 4.8 and extracted with ethyl acetatepentane 1:1.

After percolation through an acid silica gel column, 0.21 g were obtained of ω-trinor-17-cyclohexyl-13,14-dehydro-PFG$_{2\alpha}$, $[\alpha]_D = +23.9°$, $[\alpha]_{365°} = +78.1°$ (EtOH).

EXAMPLE 10

0.53 g of 5β-(2'-chloro-3'S-hydroxy-5'-cyclopentyl-pent-1'-trans-1'-enyl)-2α,4α-dihydroxy-cyclopentan-1α-ethanal-γ-lactol-3',4-bis-DIOX-ether in 8 ml of acetone and 8 ml of 0.2 N oxalic acid was refluxed for 1 hour and 30 minutes. After evaporation of the acetone in vacuo and extraction with ethyl acetate, 0.36 g were obtained of 5β-(2'-chloro-3'S-hydroxy-5'-cyclopentyl-pent-1'-trans-1'-enyl)-2α,4α-dihydroxy-cyclopentane-1α-ethanal-γ-lactol. By treatment with 3 mg of p-toluen-sulfonic acid in benzene 3 ml of methyl orthoformate, under the conditions outlined in Example 10, 0.34 g. of the lactol-methyl ether were obtained.

Under nitrogen, a solution of 90 mg of 80% NaH in mineral oil in 4 ml of DMSO was heated at 60° C. for 3 hours, until all the hydrogen had evolved. To the cooled solution of the carbanion $CH_3-SO-CH_2(-)$ obtained in this way was added a solution of the lactol-methyl ether in 1.5 ml of DMSO. This was left for 12 hours at room temperature then heated for 2 hours to 40° C., cooled, and diluted with water. It was then extracted with ethyl ether.

The organic phases were washed until neutral, dried, and the solvent removed by evaporation, to give 0.29 g of 5β-(3'S-hydroxy-5'-cyclopentyl-pent-1'-ynyl)-cyclopentane-2α,4α-dihydroxy-1α-ethanal-γ-lactol-methyl ether..

This compound was deacetalated with THF 0.2 N oxalic acid under reflux, yielding 0.24 g of the free lactol, which was then reacted with 2.5 molar equivalent of the ylide of 5-triphenyl-(4-carboxybutyl)-phosphonium bromide in DMSO, to give, after chromatography on silicic acid gel, 0.21 g of ω-trinor-17-cyclopentyl-13,14-dehydro-PGF$_{2\alpha}$, $[\alpha]_D = +20°$ (EtOH).

EXAMPLE 11

1-bromo-propane (125 mg) was added to a solution of 0.52 g of ω-trinor-17-cyclohexyl-13,14-dehydro-PGF$_{2\alpha}$-11,15-bis-THP-ether in 1.5 ml of hexamethyl-phosphorotriamide which previously had been stirred for 1 hour with 0.09 ml of 50% NaOH (w/v).

After additional stirring for 6 hours at room temperature the mixture was diluted with water (4 vol.), extracted with ether, which was washed with water until neutral and evaporated to yield 0.51 g. of ω-trinor-cyclohexyl-13,11-dehydro-PGF$_{2\alpha}$11,15-bis-THP-ether-propylester, $[\alpha]_D = -6°$ (CHCl$_3$). By the same procedure, starting with one of the bis-acetalic ethers such as those in Examples 1–10, reaction with the appropriate alkyl halogenide or alkyl sulfate, the corresponding esters were prepared.

EXAMPLE 12

An acetonic solution of an ester of a 9α,11α,15-trihydroxy-ω-nor-prost-5-en-13-ynoic acid-11,15-bis-acetalic ether obtained by the method of Example 11 [for example a solution of ω-trinor-17-cyclohexyl-13,14-dehydro-PGF$_{2\alpha}$-11,15-bis-THP-ether-propyl ester (0.15 g) in acetone (10 ml)] was refluxed with 0.2 N aqueous oxalic acid (8 ml) for 1 hour and 30 minutes. The acetone was removed in vacuum and the aqueous phase was repeatedly extracted with ether. The combined organic layers were washed until neutral dried and evaporated to dryness affording the corresponding 9α,11α,15-trihydroxy-ω-nor-prost-5-en-13-ynoic acid alkyl esters, after chromatographic purification on silica gel, using methylene chloride-ethyl acetate 80:20 as eluent.

In this way, for example, ω-trinor-17-cyclohexyl-13,14-dehydro-PGF$_{2\alpha}$-propyl ester ($[\alpha]_D = +19°$ (CHCl$_3$), 95 mg) was prepared.

EXAMPLE 13

A solution of a 9α,11α,15-trihydroxy-ω-nor-prost-13-ynoic acid-11,15-bis-acetalic ether (as, for example, 0.23 g of ω-trinor-17-cyclohexyl-13,14-dehydro-PGF,$_{2\alpha}$-11,15-bis-THP-ether) in dry pyridine (1.8 ml) was treated with 115 mg of propionic anhydride overnight at room temperature. The reaction mixture was partitioned between ethyl ether and a 30% aqueous solution of citric acid. The organic phases were combined, washed until neutral and evaporated to dryness. The resulting 9α,11α,15-trihydroxy-ω-nor-prost-13-ynoic acid-11,15-bis-acetalic ether-9-acyloxy (in the example, ω-trinor-17-cyclohexyl-13,11-dehydro-PGF$_{2\alpha}$-9-propionate-11,15-bis-THP-ether) was then deacetalated in acetone-0.2 N oxalic acid, extracted with ethyl acetate and the reaction product chromatographed on silicic acid gel (10 g:g of acid) eluted with cyclohexane-ethyl ether, yielding the 9α,11α,15-trihydroxy-ω-nor-prost-5-en-13-ynoic acid-9-acyloxy [in the example, 185 mg of ω-trinor-cyclohexyl-13,14-dehydro-PGF$_{2\alpha}$-9-propionate, $[\alpha]_D = +1°$ (CHCl$_3$)].

EXAMPLE 14

A solution of 0.36 g of 5c-9α,11α,15S-trihydroxy-18,19,20-trinor-17-cyclohexyl-prost-5-en-13-ynoic acid-propyl ester-11,15-bis-THP-ether in 18 ml of acetone was cooled to −15° and then treated with 0.8 ml of Jones' reagent, added over 4 minutes. The reaction mixture was allowed to warm up to −10° to −8° C. and kept for 20 minutes at that temperature. After dilution with benzene (108 ml) the organic phase was repeatedly washed with saturated (NH$_4$)$_2$SO$_4$ until neutral, dried and evaporated to dryness, yielding 0.35 g of 5c-9-oxo-11α,15S-dihydroxy-18,19,20-trinor-17-cyclohexyl-prost-5-en-13-ynoic acid propyl ester-11,15-bis-THP-ether.

A solution of this crude product in acetone (15 ml) was deacetalated by treatment for 8 hours at 33°–40° C., with an aqueous 0.2 N solution of oxalic acid (16 ml). After the removal of the acetone in vacuo, the aqueous phase was extracted with ethyl ether; the combined ether extracts were washed until neutral, dried and evaporated to dryness. The residue (0.34 g) was chromatographed on silica gel eluted with methylene chloride and with methylene chloride-ethyl acetate 80:20, affording 0.21 g of 5c-9-oxo-11α,15S-dihydroxy-18,19,20-trinor-17-cyclohexyl-prost-5-en-13-ynoic acid propyl ester [ω-trinor-17-cyclohexyl-13,14-dehydro-PGE$_2$-propyl ester, $[α]_D = -45°$ (CHCl$_3$)].

EXAMPLE 15

A solution of 0.3 g of 5c-9α,11α,15S-trihydroxy-18,19,20-trinor-17-cyclohexyl-16(S,R)-methyl-prost-5-en-13-ynoic acid-11,15-bis-DIOX-ether in 12 ml of acetone was cooled to −15° C. and 0.6 ml of Jones' reagent were added dropwise. It was allowed to warm up to −10° to −8° C. and kept there for 20 minutes, then diluted with 50 ml of benzene. The benzene was washed repeatedly with 30% ammonium sulfate until neutral, dried on sodium sulfate and evaporated to dryness, yielding 0.3 g of 9-oxo-11α,15S-dihydroxy-18,19,20-trinor-17-cyclohexyl-16(S,R)-methyl-prost-5-en-13-ynoic acid-11,15-bis-DIOX-ether. A solution of 0.15 g of this compound in 10 ml of tetrahydrofuran were treated with 12 ml of 0.2 N oxalic acid for 7 hours at 38° C. The THF was removed by vacuum (water bath temperature under 40°) and the aqueous phase extracted with ethyl acetate. The combined organic extracts were washed until neutral, dried and evaporated to dryness. The residue was chromatographed on silicic acid gel eluted with CH$_2$Cl$_2$-ethyl acetate 80:20, to give 85 mg of 5cis-9-oxo-11α,15S-dihydroxy-18,19,20-trinor-17-cyclohexyl-16(S,R)-methyl-prost-5-en-13-ynoic acid [ω-trinor-17-cyclohexyl-16 (R,S)-methyl-13,14-dehydro-PGE$_2$, $[α]_D = 48°$ (EtOH)].

EXAMPLE 16

To a solution of 0.15 g of 5c-9α,11α,15S-trihydroxy-18,19,20-trinor-17-cyclopentyl-prost-5-en-13-ynoic acid-11,15-bis-THP-ether (as in example 8) in 6 ml of acetone, cooled to −12° was added, with stirring, 0.3 ml of Jones' reagent. After 15 minutes at −10° it was diluted with 30 ml of benzene. The organic phase was washed with saturated ammonium sulfate until neutral, dried over MgSO$_4$ and evaporated to dryness.

A solution of the resulting 5c-9-oxo-11α,15S-dihydroxy-18,19,20-trinor-17-cyclopentyl-prost-5-en-13-ynoic acid-11,15-bis-THP-ether in acetone (8 ml) was deacetalated by reaction at 38° with 0.2 N oxalic acid (9 ml). The acetone was pulled off in a rotating vacuum evaporator and the aqueous phase was extracted with ethyl ether. The combined ether extracts were washed until neutral, dried on MgSO$_4$ and evaporated to dryness. The residue (0.13 g) was chromatographed on 1.5 g of acid-washed silica gel, eluted with methylene chloride-ethyl acetate 80:20, to give 56 mg of ω-trinor-17-cyclopentyl-13,14-dehydro-PGE$_2$, $[α]_D = 41°$ (EtOH).

EXAMPLE 17

0.25 g of 5c-9α,11α,15R-trihydroxy-18,19,20-trinor-17-cyclohexyl-16S-methyl-prost-5-en-13-ynoic acid-11,15-bis-THP-ether was oxidized in acetone with Jones' reagent to give the corresponding 9-oxo-derivative. This was deacetalated with acetone-0.2 N oxalic acid at 38° C. and after chromatography on silicic acid gel, 0.11 g of ω-trinor-17-cyclohexy-16S-methyl-15-epi-13,14-dehydro-PGE$_2$, $[α]_D = -41°$ (EtOH) was obtained.

EXAMPLE 18

Starting from one of the 11,15-bis-acetalic ethers (11,15-bis-DIOX-ether, 11,15-bis-THP-ether) of a 9α,11α,15S or a 9α,11α,15R-trihydroxy-prost-5-en-13-ynoic acid, either as the free acid or as one of the esters described in examples 1 to 8 and 11, oxidation in acetone with Jones' reagent, by the procedures described in example 14 to 17, afforded the corresponding (free or esterified), 9-oxo-prost-13-ynoic acid, 11,15-bis-acetalic ethers, 11,15-bis-DIOX-ether or 11,15-bis-THP-ether, which were then deacetalated as described in the procedure of preceding examples, to give:

ω-trinor-17-cyclohexyl-13,14-dehydro-PGE$_2$, $[α]_D = -51°$ (EtOH);

ω-trinor-17-cyclohexyl-13,14-dehydro-15-epi-PGE$_2$, $[α]_D = -47°$ (EtOH);

ω-trinor-17-cyclohexyl-16(S,R)-methyl-13,14-dehydro-PGE$_2$;

ω-trinor-17-cyclohexyl-16S-methyl-13,14-dehydro-PGE$_2$;

ω-trinor-17-cyclohexyl-16R-methyl-13,14-dehydro-PGE$_2$;

ω-trinor-17-cyclohexyl-16S-methyl-13,14-dehydro-15-epi-PGE$_2$; $[α]_D = -41°$ (EtOH);

ω-trinor-17-cyclohexyl-16R-methyl-13,14-dehydro-15-epi-PGE$_2$;

ω-trinor-17-(2'-nor-bornyl)-13,14-dehydro-PGE$_2$;

ω-trinor-17-(2'-tetrahydrofuryl)-13,14-dehydro-PGE$_2$;

ω-trinor-17-(1'-adamantyl)-13,14-dehydro-PGE$_2$;

107   -trinor-17-(2'-bicyclo[2,2,2]octyl-13,14-dehydro-PGE$_2$;

ω-trinor-17-cycloheptyl-13,14-dehydro-PGE$_2$;

ω-trinor-17-(4'-tert-butyl-cyclohexyl)-13,14-dehydro-PGE$_2$;

ω-trinor-17-cyclopropyl-13,14-dehydro-PGE$_2$;

ω-trinor-17-cyclopentyl-13,14-dehydro-PGE$_2$;

ω-trinor-17-cyclopentyl-16S-methyl-13,14-dehydro-PGE$_2$;

ω-trinor-17-cyclopentyl-16R-methyl-13,14-dehydro-PGE$_2$;

ω-tetranor-16-cyclohexyl-13,14-dehydro-PGE$_2$;

ω-tetranor-16-cyclopentyl-13,14-dehydro-PGE$_2$;

ω-tetranor-16-(1'-adamantyl)-13,14-dehydro-PGE$_2$;

ω-dinor-18-cyclohexyl-13,14-dehydro-PGE$_2$.

EXAMPLE 19

A solution of 0.3 g of 5c-9-oxo-11α,15S-dihydroxy-18,19,20-trinor-17-cyclohexyl-prost-5-en-13-ynoic acid-11,15-bis-THP-ether methyl ester in 40 ml of acetone and 50 ml of 0.2 N aqueous oxalic acid was refluxed for 6 hours. The acetone was removed under vacuum and the aqueous phase extracted with ethyl ether. The combined ether extracts were washed until neutral, dried and the ether evaporated in vacuo to afford, after thin-layer chromatography (cyclohexane-ether), 0.12 g of 5c-15S-hydroxy-9-oxo-18,19,20-trinor-17-cyclohexyl-prosta-5,10-dien-13-ynoic acid-methyl ester (ω-trinor-17-cyclohexyl-13,14-dehydro-PGA$_2$).

EXAMPLE 20

A solution of 5c-11α,15S-dihydroxy-9-oxo-18,19,20-trinor-17-cyclopentyl-16S-methyl-prost-5-en-13-ynoic acid-11,15-bis-THP-ether (0.4 g) in 40 ml of acetone was treated with 40 ml of 0.25 N oxalic acid for 6 hours under reflux. The acetone was removed in vacuo and the aqueous phase extracted repeatedly with ether. The combined ether extracts were washed with saturated ammonium sulfate solution and dried, yielding, after preparative thin-layer chromatography of the residue on silica gel plates (using benzene-ethyl acetate-acetic acid 130:24:6 as eluent), 5c-15S-hydroxy-9-oxo-18,19,20-trinor-17-cyclopentyl-16S-methyl-prosta-5,10-dien-13-ynoic acid.

EXAMPLE 21

Usin the procedures described in examples 19 and 20, the 5c-9-oxo-prost-5-en-13-ynoic acid-11,15-bis-acetalic ethers (both free acids and esters) of example 18 were deacetalated at reflux temperatures (65°–70° C.) with acetone-0.25 N aqueous oxalic acid to give the esters and the free acids of the following compounds:

ω-trinor-17-cyclohexyl-13,14-dehydro-PGA$_2$;
ω-trinor-17-cyclohexyl-13,14-dehydro-15-epi-PGA$_2$;
ω-trinor-17-cyclohexyl-16(S,R)-methyl-13,14-dehydro-PGA$_2$;
ω-trinor-17-cyclohexyl-16S-methyl-13,14-dehydro-PGA$_2$;
ω-trinor-17-cyclohexyl-16R-methyl-13,14-dehydro-PGA$_2$;
ω-trinor-17-cyclohexyl-16S-methyl-13,14-dehydro-15-epi-PGA$_2$;
ω-trinor-17-cyclohexyl-16R-methyl-13,14-dehydro-15-epi-PGA$_2$;
ω-trinor-17-(2'-nor-bornyl)-13,14-dehydro-PGA$_2$;
ω-trinor-17-(2'-tetrahydrofuryl)-13,14-dehydro-PGA$_2$;
ω-trinor-17-(1'-adamantyl)-13,14-dehydro-PGA$_2$;
107  -trinor-17-(2'-bicyclo[2,2,2]octyl)-13,14-dehydro-PGA$_2$;
ω-trinor-17-cycloheptyl-13,14-dehydro-PGA$_2$;
ω-trinor-17-(4'-tert-butyl-cyclohexyl)-13,14-dehydro-PGA$_2$;
ω-trinor-17-cyclopropyl-13,14-dehydro-PGA$_2$;
ω-trinor-17-cyclopentyl-13,14-dehydro-PGA$_2$;
ω-trinor-17-cyclopentyl-16S-methyl-13,14-dehydro-PGA$_2$;
ω-trinor-17-cyclopentyl-16S-methyl-13,14-dehydro-PGA$_2$;
ω-tetranor-16-cyclohexyl-13,14-dehydro-PGA$_2$;
ω-tetranor-16-cyclopentyl-13,14-dehydro-PGA$_2$;
ω-tetranor-16-(1'-adamantyl)-13,14-dehydro-PGA$_2$;
ω-dinor-18-cyclohexyl-13,14-dehydro-PGA$_2$.

EXAMPLE 22

To a solution of 13.1 g of dimethyl-(2-oxo-4-cyclohexyl)-butyl-phosphonate in 200 ml of tetrahydrofuran were added 27.28 g of pyrrolidone-2-hydrotribromide (PHT). The reaction mixture was left overnight with stirring. The precipitate which separated out was filtered off, the THF was evaporated under vacuum (bath temperature below 30°) and the residue taken up in ethyl ether, which was washed until neutral.

After drying and evaporation of the ether, the residue was chromatographed on silica gel, eluted with cyclohexane-ethyl ether to obtain 9.32 g of dimethyl-(1-bromo-2-oxo-4-cyclohexyl)-butyl phosphonate.

Bromine: found 23.18, calculated 23.42.

EXAMPLE 23

With exclusion of humidity to a stirred suspension of 2.1 g of sodium hydride (80% dispersion in mineral oil) in 60 ml of dry benzene was added, dropwise, a solution of 18.34 g of dimethyl-(2-oxo-4-cyclohexyl)-butyl phosphonate.

Stirring was continued until all the hydrogen had evolved. Then 9.65 g of N-chloro succinimide was added and the mixture stirred for 1 hour.

The reaction mixture was washed with a solution of 5% NaH$_2$PO$_4$, a solution of 7% KI and 7% sodium thiosulfate, and then with water until neutral. After drying and evaporating the solvent, the residue was purified by distillation, giving 11.2 g of dimethyl-(1-chloro-2-oxo-4-cyclohexyl)-butyl phosphonate, b.p. 120°–126° (1.2 mm Hg).

EXAMPLE 24

A solution of 10 g of dimethyl-(2-oxo-4-cyclopentyl)-butyl-phosphonate in 10 ml of acetic acid was cooled in an ice and water bath and, with stirring, 2 drops of a solution of HBr in acetic acid were added and then, dropwise, a solution of 6.5 g of bromine in 3 ml of acetic acid, was added until a faint color persisted. The mixture was then diluted with 2 vol. of water and extracted with dichloromethane, which was washed with saturated ammonium sulfate solution until neutral, dried and evaporated to dryness. The residue was purified by chromatography on a silica gel column, giving 7.4 g of dimethyl-(1-bromo-2-oxo-4-cyclopentyl)-butyl-phosphonate. Bromine: found 24.32, calculated 24.30.

EXAMPLE 25

To a suspension of 30 mg of 80% NaH in 4 ml of benzene was added dropwise a solution of 297 mg of dimethyl-(1-chloro-2-oxo-4-cyclohexyl)-butyl-phosphonate in 4 ml of benzene and stirring continued until no more hydrogen evolved. Then 184 mg of 5β-formyl-2α,4α-dihydroxy-cyclopentane-1α-acetic acid-γ-lactone-4-acetone in benzene was added. After stirring for 15 minutes, it was filtered and the filtrate washed with a 5% solution of NaH$_2$PO$_4$ and water until neutral, dried and evaporated to dryness. The residue was chromatographed on silica gel, eluted with CH$_2$Cl$_2$-ethyl ether 95:5, yielding 240 mg of 5β-(2'-chloro-3'-oxo-5'-cyclohexyl-pent-1'-trans-1'-enyl)-2α,4α-dihydroxy-cyclopentane-1α-acetic acid-γ-lactone-4-acetate (λ max 242 mμ, ε=9,900).

EXAMPLE 26

To a stirred solution of 68 mg of sodium ethylate in 10 ml of dimethoxyethane, were added 340 mg of dimethyl-(1-bromo-2-oxo-4-cyclohexyl)-butyl-phosphonate, and stirring was continued until all the reagent had dissolved. Then a solution of 5β-formyl-2α,4α-dihydroxy-cyclopentane-1α-acetic acid-γ-lactone-4-acetate (185 mg) in benzene was added.

After stirring for 30 minutes, it is diluted with a 5% solution of NaH$_2$PO$_4$ in water.

The organic phase was washed until neutral and evaporated to dryness. The residue, after purification on silica gel (CH$_2$Cl$_2$-ether 95:5) gave 282 mg of 5β-(2'-bromo-3'-oxo-5'-cyclohexyl-pent-1'-trans-1'-enyl)-2α,4α-dihydroxy-cyclopentane-1α-acetic acid-γ-lactone-4-acetate (λ max 251 mμ, ε=11,700).

EXAMPLE 27

A stirred suspension of 15 mg of NaH (80% dispersion in mineral oil) in 1.5 ml of DMSO was heated to 60° until no more hydrogen evolved. The solution of the carbanion CH$_3$—SO—CH$_2$$^{(-)}$ obtained in this way was cooled to 10°–12° and diluted with 4 ml of anhydrous benzene. To this was then added a solution of 165 mg of dimethyl-(1-bromo-2-oxo-4-cyclopentyl)-butyl-phosphonate in benzene and stirring was continued for 30 minutes. To this mixture was then added a benzene solution of 92 mg of 5β-formyl-2α,4α-dihydroxy-cyclopentane-1α-acetic acid-γ-lactone-4-acetate and stirring continued for 20 minutes. The reaction mixture was diluted with 25 ml of benzene, washed with 5% NaH$_2$PO$_4$ and water until neutral, dried and the solvent evaporated off.

After chromatography on silica gel (methylene chloride-ether 96:4) the residue yielded 120 mg of 5β-(2'-bromo-3'-oxo-5'-cyclopentyl-pent-1'-trans-1'-enyl)-2α,4α-dihydroxy-cyclopentane-1α-acetic acid-γ-lactone-4-acetate (λ max 252 mμ, ε=10,950).

EXAMPLE 28

Following the procedure of example 22, 16.5 g of dimethyl-(2-oxo-4-(2'-nor-bornyl)-butylphosphonate in 250 ml of anhydrous tetrahydrofuran were treated with 32.8 g of pyrrolidone-2-hydrotribromide to give 17.2 g of dimethyl-(1-bromo-2-oxo-4-(2'-nor-bornyl)-butyl-phosphonate. Under nitrogen, to a solution of 354 mg of this phosphonate in toluene cooled to −15° C. was added, dropwise, with stirring 1 molar equivalent of a solution of butyl lithium in heptane, which is stirred until gas evolution ceases.

The mixture is warmed to 0°–5° and a solution of 180 mg of 5β-formyl-2α,4α-dihydroxy-cyclopentan-1α-acetic acid-γ-lactone-4-acetate in benzene is added. Stirring is continued for another 20 minutes, then the mixture is diluted with 5% aqueous NaH$_2$PO$_4$, the organic phase is separated, washed until neutral, dried and the solvent removed by evaporation. After purification on silica gel, 210 mg of 5β-(2'-bromo-3'-oxo-5-(2'-nor-bornyl)-pent-1'-trans-1'-enyl)-2α,4α-dihydroxy-cyclopentane-1α-acetic acid-γ-lactone (λ max 251 mμ, ε=11,000) were obtained.

EXAMPLE 29

Under inert gas, 72 mg of NaH (80% dispersion in mineral oil) in 3 ml of DMSO were heated with stirring to 60° until no more hydrogen evolved.

The solution was cooled to 10°–12° and diluted with 20 ml of benzene. Over a 15 minutes period, a solution of 0.75 g of dimethyl-(2-bromo-2-oxo-4-cyclohexyl)-phosphonate was added dropwise. After stirring for 30 minutes more, a solution of 0.7 g of 5β-formyl-2α,4α-dihydroxy-cyclopentane-1α-acetic acid-γ-lactone-4-p-phenylbenzoate in 15 ml of benzene was added. After 30 minutes, it was diluted with 30 ml of benzene and 30 ml of a 5% aqueous solution of NaH$_2$PO$_4$. The organic layer was separated off, washed until neutral, dried and the solvent evaporated off. After chromatographic purification on silica gel (eluent CH$_2$Cl$_2$-ether 90:10) and crystallization from ethyl ether, 0.82 g were obtained of 5β-(2'-bromo-3'-oxo-5'-cyclohexyl-pent-1'-trans-1'-enyl)-2α,4α-cyclopentane-1α-acetic acid-γ-lactone-4-p-phenylbenzoate, m.p. 155°–157° C.

EXAMPLE 30

To a suspension of 104 mg of NaH (80% dispersion in mineral oil) in 30 ml of benzene, a solution of 904 mg of dimethyl-(2-oxo-4-cyclohexyl)-butyl-phosphonate in 10 ml of benzene was added dropwise and stirred for an hour. A gelatinous suspension was formed to which was added, all at once, 614 mg of finely divided N-bromosuccinimide. After 15 minutes of stirring, a solution of 1.05 g of 5β-formyl-2α,4α-dihydroxy-cyclopentane-1α-acetic acid-γ-lactone-4-p-phenylbenzoate in 20 ml of benzene was added. The mixture was stirred for 20 minutes and then diluted with 20 ml of 6% aqueous NaH$_2$PO$_4$. The organic phase was separated, washed until neutral, dried and the solvent removed by evaporation.

After purification on a silica gel column, 1.17 g of 5β-(2'-bromo-3'-oxo-5'-cyclohexyl-pent-1'-trans-1'-enyl)-cyclopentane-2α,4α-dihydroxy-1α-acetic acid-γ-lactone-4-p-phenylbenzoate, m.p. 154°–156° C., were obtained.

A solution of 2 g of this compound in 20 ml of dimethoxyethane and 80 ml of ethyl ether was dropped into a 0.14 M Zn(BH$_4$)$_2$ ethereal solution (150 ml).

After 30 minutes the transenone lactone was completely reduced. A saturated aqueous sodium chloride solution was added to decompose the excess reagent, then 2 N H$_2$SO$_4$ to adjust the mixture to pH 3.5.

The organic phase was washed until neutral and evaporated to dryness. The residue was chromatographed on 100 g of silica gel to give by elution with cyclohexane-ethyl acetate 80:20 and then 60:40, respectively 1.245 g of 5β-(2'-bromo-3'S-hydroxy-5'-cyclohexyl-pent-1'-trans-1'-enyl)-cyclopentane-2α,4α-dihydroxy-1α-acetic acid-γ-lactone-4-p-phenylbenzoate, m.p. 124°–126° C. and 0.485 g of the 3'R-hydroxy epimer, m.p. 177°–179° C.

EXAMPLE 31

When dimethyl-(2'-oxo-3'S-methyl-4'-cyclohexyl)-butylphosphonate (950 mg) was substituted for the phosphonate used in example 30 and the halogenating reagent was N-bromo-acetamide (480 mg), reaction with the p-phenylbenzoate aldehyde gave rise to 5β-(2'-bromo-3'-oxo-4'S-methyl-5'-cyclohexyl-pent-1'-trans-1'-enyl)-2α,4α-dihydroxy-cyclopentane-1α-acetic acid-γ-lactone-4-p-phenylbenzoate, m.p. 144°–146° C.

EXAMPLE 32

Following the procedure outlined in example 30, with dimethyl-(2-oxo-3'R-methyl-cyclohexyl)-butyl-phosphonate (0.95 g) and N-bromo-caprolactam as halogenating reagent, 5β-(2'-bromo-3'-oxo-4'R-methyl-5'-cyclohexyl-pent-1'-trans-1'-enyl)-2α,4α-dihydroxy-cyclopentane-1α-acetic acid-γ-lactone-4-p-phenylbenzoate, m.p. 139–141° C. was obtained.

EXAMPLE 33

To a suspension of 72 mg of 80% NaH in benzene was added dropwise a solution of 680 mg of dimethyl-(2-oxo-4-cyclopentyl)-butyl-phosphonate in 10 ml of benzene. After stirring for 90 minutes, 370 mg of N-chlorosuccinimide were added and stirring continued for 30 minutes.

To the carbanion of the chloro-phosphonate so obtained was added a solution of 0.875 g of 5β-formylcyclopentane-2α, 4α-dihydroxy-1α-acetic acid-γ-lactone-p-phenylbenzoate in 20 ml of benzene. Stirring was continued for 20 minutes, then 5% aqueous NaH$_2$PO$_4$ was added and the organic phase was separated, washed until neutral, dried with MgSO$_4$ and evaporated to dryness. The resulting crude product (1.4 g) was chromatographed on silica gel (eluted with CH$_2$Cl$_2$), yielding 0.98 g of 5β-(2'-chloro-3'-oxo-5'-cyclopentyl-pent-1'-trans-1'-enyl)-2α,4α-dihydroxy-cyclopentane-1α-acetic acid-γ-lactone-4-p-phenylbenzoate.

This compound was characterized by NMR spectra, where the proton of H$_1$, appeared as a doublet centered at 6.75δ, with a coupling constant with the 5$_α$H proton of $J_{AB}=9$ Hz. These values were clearly different from those for the epimer cis-chlorenone in which the $H_1$ proton appeared as a doublet at 6.00δ, with a coupling constant $J_{AB}=19.2$ Hz with the $5_\alpha H$ proton.

EXAMPLE 34

In the procedure outlined in example 33, when the phosponate was replaced by the analogue dimethyl-(2-oxo-3-methyl-4-cyclopentyl)-butyl-phosphonate and the N-chloro-succinimide by N-chloro-acetamide, the product obtained was 5β-(2'-chloro-3'-oxo-4'S-methyl-5'-cyclopentyl-pent-1'-trans-1'-enyl)-2α, 4α-dihydroxy-cyclopentane-1α-acetic acid-γ-lactone-4-p-phenylbenzoate.

EXAMPLE 35

Starting with the following phosphonates:
dimethyl-(2-oxo-4-cyclohexyl)-butyl-phosphonate;
dimethyl-(2-oxo-3(S,R)-methyl-4-cyclohexyl)-butyl-phosphonate;
dimethyl-(2-oxo-3S-methyl-4-cyclohexyl)-butyl-phosphonate;
dimethyl-(2-oxo-3R-methyl-4-cylohexyl)-butyl-phosphonate;
dimethyl-[2-oxo-4-(2'-nor-bornyl)]-butyl-phosphonate;
dimethyl-[2-oxo-4-(2'-tetrahydrofuryl)]-butyl-phosphonate;
dimethyl-[2-oxo-4-(2'tetrahydrothiophenyl)]-butyl-phosphonate;
dimethyl-[2-oxo-4-(1'-adamantyl)]-butyl-phosphonate;
dimethyl-[2-oxo-4-(2-bicyclo[2,2,2]octyl)]-butyl-phosphonate;
dimethyl-(2-oxo-4-cycloheptyl)-butyl-phosphonate;
dimethyl-[1-oxo-4-(4'-tert-butyl)-cyclohexyl]-butyl-phosphonate;
dimethyl-(2-oxo-4-cyclopropyl)-butyl-phosphonate;
dimethyl-(2-oxo-4-cyclopentyl)-butyl-phosphonate;
dimethyl-(2-oxo-3S-methyl-4-cyclopentyl)-butyl-phosphonate;
dimethyl-(2-oxo-3R-methyl-4-cyclopentyl)-butyl-phosphonate;
dimethyl-(2-oxo-3-cyclohexyl)-propyl-phosphonate;
dimethyl-(2-oxo-3-cyclopentyl)-propyl-phosphonate;
dimethyl-(2-oxo-3-1'-adamantyl)-propyl-phosphonate;
dimethyl-(2-oxo-5-cyclohexyl)-pentyl-phosphonate;
and proceeding as described for examples 22, 23, 24 and 28, the corresponding 1-halogen (1-chloro and 1-bromo)-phosphonates were prepared.

EXAMPLE 36

By means of alkylization of a 4-ester, in particular the 4-p-phenylbenzoate of 5β-formyl-cyclopentane-2α,4α-dihydroxy-1α-acetic acid-γ-lactone with a bromo phosphonate, using one of the methods described in examples 25 to 34, either using one of the halogen phosphonates described in example 35, or generating the halogen phosphonate in situ by reaction with a convenient N-bromo-imide, the following 2α,4α-dihydroxy-cyclopentane-1α-acetic acid-γ-lactone-4-esters, particularly the 2α,4α-dihydroxy-cyclopentane-1α-acetic acid-γ-lactone-4-p-phenylbenzoate were prepared:
5β-(2'-bromo-3'-oxo-5'-cyclohexyl-pent-1'-trans-1'-enyl);
5β-(2'-bromo-3'-oxo-4'(S,R)-methyl-5'-cyclohexyl-pent-1'-trans-1'-enyl);
5β-(2'-bromo-3'-oxo-4'S-methyl-5'-cyclohexyl-pent-1'-trans-1'-enyl);
5β-(2'-bromo-3'-oxo-4'R-methyl-5'-cyclohexyl-pent-1'-trans-1'-enyl);
5β-(2'-bromo-3'-oxo-5'-(2'-nor-bornyl)-pent-1'-trans-1'-enyl);
5β-(2'-bromo-3'-oxo-5'-(2'-tetrahydrofuryl)-pent-1'-trans-1'-enyl);
5-(2'-bromo-3'-oxo-5'-(2'-tetrahydrothiophenyl)-pent-1'-trans-1'-enyl);
5β-(2'-bromo-3'-oxo-5'-adamantyl-pent-1'-trans-1'-enyl);
5β-(2'-bromo-3'-oxo-5'-bicyclo[2,2,2]octyl-pent-1'-trans-1'enyl);
5β-(2'-bromo-3'-oxo-5'-cyclopentyl-pent-1'-trans-1'-enyl);
5β-(2'-bromo-3'-oxo-5'-cyclopropyl-pent-1'-trans-1'-enyl);
5β-(2'-bromo-3'-oxo-5'-(4'-tert-butyl)-cyclohexyl-pent-1'-trans-1'-enyl);
5β-(2'-bromo-3'-oxo-5'-cyclopentyl-pent-1'-trans-1'-enyl);
5β-(2'-bromo-3'-oxo-4'S-methyl-5'-cyclopentyl-pent-1'-trans-1'-enyl);
5β-(2'-bromo-3'-oxo-4'S-methyl-5'-cyclopentyl-pent-1'-trans-1'-enyl);
5β-(2'-bromo-3'-oxo-4'R-methyl-5'-cyclopentyl-pent-1'-trans-1'-enyl);
5β-(2'-bromo-3'-oxo-4'-cyclohexyl-but-1'-trans-1'-enyl), m.p. 184°–185° C.;
5β-(2'-bromo-3'-oxo-4'-cyclopentyl-but-1'-trans-1'-enyl);
5β-(2'-bromo-3'-oxo-4'-adamantyl-but-1'-trans-1'-enyl);
5β-(2'-bromo-3'-oxo-6'-cyclohexyl-hex-1'-trans-1'-enyl), m.p. 148°–149° C.

All these compounds were characterized by their NMR spectra, in which the olefinic proton appeared as a doublet centered around 6.94δ, with a coupling constant $J_{AB}=9$ Hz with the $5_\alpha$proton of the cyclopentane ring. In the geometric bromo-cis-enone isomers the same olefinic proton showed itself as a doublet centered at 6.18δ, with a coupling constant $J_{AB}=10.2$ Hz.

EXAMPLE 37

To a stirred solution of 0.05 M zincborohydride in ether (250 ml), were added a solution of 2.4 of 5β-(2'-chloro-3'-oxo-4'S-methyl-cyclopentyl-pent-1'-trans-1'-enyl)-2α,4α-dihydroxy-cyclopentane-1α-acetic acid-γ-lactone-4-p-phenylbenzoate dissolved in 30 ml of dimethoxyethane. 30 minutes after the last portion of reagent was added, the excess reagent was destroyed by careful addition of a saturated NaCl solution. The precipitate of Zn(OH)₂ was dissolved by acidification with 2 N sulfuric acid and the organic phase was separated off, washed until neutral, dried and the solvent removed under vacuum. The residue was chromatographed on 450 g of silica gel eluted with methylene chloride-ethyl ether to give 1.24 g of 5β-(2'-chloro-3'S-hydroxy-4'S-methyl-5'-cyclopentyl-pent-1'-trans-1'-enyl)-2α,4α-dihydroxy-cyclopentane-1α-acetic acid-γ-lactone-4-p-phenylbenzoate and 0.61 g of the 3'R epimeric alcohol.

EXAMPLE 38

Sodium borohydride (80 mg) was added under stirring to a solution of 5β-(2'-chloro-3'-oxo-5'-cyclopentyl-pent-1'-trans-1'-enyl)-2α,4α-dihydroxy-cyclopentane-1α-acetic acid-γ-lactone-4-p-phenylbenzoate (0.4 g) in 10 ml of methanol and 5 ml of methylene chloride cooled to −5° to −10° C. After stirring for 30 minutes at that temperature, the excess reagent was destroyed by addition of 15% aqueous acetic acid and the mixture evaporated in vacuo. The residue was taken up in water-methylene chloride and the organic layer washed until neutral and evaporated to dryness. The crude product, a mixture of the two 3'S and 3'R epimeric alcohols, was chromatographed on 80 g of silica gel. Elution with ether-isopropyl ether 75:25 gave 0.15 g of 5β-(2'-chloro-3'S-hydroxy-5'-cyclopentyl-pent-1'-trans-1'-enyl)-2α,4α-dihydroxy-cyclopentan-1α-acetic acid-γ-lactone-4-p-phenylbenzoate and 0.1 g of the 3'R alcohol.

EXAMPLE 39

When, in the procedure outlined in example 38, the transenone derivative was replaced with 5β-(2'-bromo-3'-oxo-5'-(2'-tetrahydrofuryl)-pent-1'-trans-1'-enyl)-2α,4α-dihydroxy-cyclopentane-1α-acetic acid-γ-lactone-4-p-phenylbenzoate, both of the epimeric alcohols were obtained, which after elution from a silica gel column with methylene chloride-ethyl ether 90:10 yields 0.10 g of 5β-(2'-bromo-3'R-hydroxy-5'-(2'-tetrahydrofuryl)-pent-1'-trans-1'-enyl)-2α,4α-dihydroxy-cyclopentane-1α-acetic acid-γ-lactone-4-p-phenylbenzoate and 0.21 g of the epimeric 3'S alcohol. A stirred solution of 0.7 g of this compound in 30 ml of anhydrous methanol was treated with 210 mg of K₂CO₂ at room temperature, for 4 hours and then neutralized by addition of 15% aqueous acetic acid. The methanol was removed under vacuum and the residue partitioned between ethyl acetate and 10% aqueous sodium chloride. The organic layer was separated, washed until neutral, dried and the solvent evaporated off to give the free dihydroxy-lactone:

5β-(2'-bromo-3'S-hydroxy-5-(2'-tetrahydrofuryl)-pent-1'-trans-1'-enyl)-2α,4α-dihydroxy-cyclopentane-1α-acetic acid-γ-lactone (0.49 g).

To a solution of this compound in 20 ml of anhydrous benzene was added 0.35 of 2,3-dihydropyran and a solution in benzene of 2.5 mg of p-toluene-sulfonic acid. The mixture was maintained at room temperature for 3 hours, then washed with 3% aqueous potassium carbonate and then with after until neutral. After removal of the solvent in vacuo, the residue was chromatographed on silica gel and eluted with cyclohexane ethyl acetatepyridine 80:20:0.1 to give 0.675 g of pure 5β-(2'-bromo-3'S-hydroxy-5-(2'-tetrahydrofuryl)-pent-1'-trans-1'-enyl)-1α,4α-dihydroxy-cyclopentan-1α-acetic acid-γ-lactone-3'S,4α-bis-THP-ether.

EXAMPLE 40

A stirred solution of 1.3 g of 5β-(2'-bromo-3'-oxo-4'S-methyl-5'-cyclohexyl-pent-1'-trans-1'-enyl)-2α,4α-dihydroxy-cyclopentane-1α-acetic acid-γ-lactone-4-p-phenylbenzoate in 20 ml of CH₂Cl₂ and 25 ml of methanol, cooled to −10°, was treated with 120 mg of NaBH₄ and left for 30 minutes at 0°–2° C. to obtain complete reduction of the keto group. After neutralization with 15% aqueous acetic acid and solvent evaporation under vacuum, the residue was transferred to a silica gel column (250 g) with methylene chloride and eluted with methylene chloride containing increasing amounts of ethyl ether. The first product to be eluted was 0.72 g of 5β-(2'-bromo-3'-S-hydroxy-4'S-methyl-5'-cyclohexyl-pent-1'-trans-1'-enyl)-2α,4α-dihydroxy-cyclopentane-1α-acetic acid-γ-lactone-4-p-phenylbenzoate and the second was 0.36 g of the epimeric 3'S-alcohol.

The 3'S-alcohol was then treated in methanol (25 ml) with 6 ml of an aqueous 20% solution of K₂CO₃, for one hour under reflux. The reaction mixture was cooled, acidified to pH 1 and left for 2 hours at room temperature. The salts, which precipitated out, were removed by filtration and the filtrate concentrated in vacuo to a small volume which was extracted with methylene chloride-ethyl acetate to give 0.46 g of 5β-(2'-bromo-3'S-hydroxy-4'S-methyl-5'-cyclohexyl-pent-1'-trans-1'-enyl)-2α,4α-dihydroxy-cyclopentane-1α-acetic acid-γ-lactone.

A solution of this product in anhydrous benzene was reacted with 0.4 g of 1,4-diox-2-ene and 4 mg of anhydrous p-toluensulfonic acid, for 3 hours at room temperature. The organic phase was washed with 5% potassium carbonate and with water until neutral, dried and evaporated to dryness to yield 0.68 g of 5β-(2'-bromo-3'S-hydroxy-4'S-methyl-5'-cyclohexyl-pent-1'-trans-1'-enyl)-2α,4α-dihydroxy-cyclopentane1α-acetic acid-γ-lactone-3',4-bis-DIOX-ether.

EXAMPLE 41

Starting with the 1'-trans-2-halo-3'-oxo-ketones such as in example 36 and earlier ones, working according to the procedures described in examples 30, 37, 38, 39 and 40, the reduction of the α-haloenone group, either with a solution of zinc borohydride in ether or with sodium borohydride in methanol, gave rise to the epimeric 2'-halo-3'S-hydroxy and 2'-halo-3'R-hydroxy alcohols that were separated on column to give the individual epimeric 4-ester derivatives, which were then saponified to give the corresponding bicyclic lactone-3',4-dihydroxy-derivatives, then reacted with 2,3-dihydropyran or 1,4-diox-2-ene to give the following 2α,4α-dihydroxy-cyclopentane-1α-acetic acid-γ-lactones:

5β-(2'-chloro-3'S-hydroxy-4'(S,R)-methyl-5'-cyclopentyl-pent-1'-trans-1'-enyl);

5β-(2'-chloro-3'S-hydroxy-5'-cyclopentyl-pent-1'-trans-1'-enyl);

5β-(2'-bromo-3'S-hydroxy-5'-cyclohexyl-pent-1'-trans-1'-enyl);

5β-(2'-bromo-3'S-hydroxy-4'(S,R)-methyl-5'-cyclohexyl-pent-1'-trans-1'-enyl);

5β-(2'-bromo-3'S-hydroxy-4'S-methyl-5'-cyclohexyl-pent-1'-trans-1'-enyl);

5-(2'-bromo-3'S-hydroxy-1''R-methyl-5'-cyclohexyl-pent-1'-trans-1'-enyl);

5β-(2'-bromo-3'S-hydroxy-5(-(2''-nor-bornyl)-pent-1'-trans-1'-enyl);

5β-(2'-bromo-3'-S-hydroxy-5'-(2''-tetrahydrofuryl)-pent-1'-trans-1'-enyl);

5β-(2'-bromo-3'S-hydroxy-5'-(2''-tetrahydrothiophenyl)-pent-1'-trans-1'-enyl);

5β-(2'-bromo-3'S-hydroxy-5'-(adamantyl)-pent-1'-trans-1'-enyl);

5β-(2'-bromo-3'S-hydroxy-5'-bicyclo[2,2,2]octyl-pent-1'-trans-1'-enyl);

5β-(2'-bromo-3'S-hydroxy-5'-cycloheptyl-pent-1'-trans-1'-enyl);

5β-(2'-bromo-3'S-hydroxy-5'-cyclopropyl-pent-1'-trans-1'-enyl);

5β-(2'-bromo-3'S-hydroxy-5'-(4-tert-butyl)-cyclohexyl-pent-1'-trans-1'-enyl);

5β-(2'-bromo-3'S-hydroxy-5'-cyclopentyl-pent-1'-trans-1'-enyl);

5β-(2'-bromo-3'S-hydroxy-4'S-methyl-5'-cyclopentyl-pent-1'-trans-1'-enyl);

5β-(2'-bromo-3'S-hydroxy-4'R-methyl-5'-cyclopentyl-pent-1'-trans-1'-enyl);

5β-(2'-bromo-3'S-hydroxy-4'-cyclohexyl-but-1'-trans-1'-enyl);

5β-(2'-bromo-3'S-hydroxy-4'-cyclopentyl-but-1'-trans-1'-enyl);

5β-(2'-bromo-3'S-hydroxy-4'-adamantyl-but-1'-trans-1'-enyl);

5β-(2'-bromo-3'S-hydroxy-6'-cyclohexyl-hex-1'-trans-1'-enyl);

and their 3'R epimeric alcohols, either as the 4-esters (particularly the 4-p-phenylbenzoate) or as the free 3',4-diols and their 3',4-bis-THP-ethers and 3',4-bis-DIOX-ethers.

EXAMPLE 42

A solution of 7.2% DIBA in toluene (16 ml) was added over a 15 minute period to a stirred solution of 5β-(2'-chloro-3'S-hydroxy-4'(S,R)-methyl-5'-cyclopentyl-pent-1'-trans-1'-enyl)-2α,4α-dihydroxy-cyclopentane-1αacetic acid-γ-lactone-3',4-bis-DIOX-ether (1.1 g) in dry toluene, cooled to −60°.

Stirring was continued for 30 minutes, then the reaction mixture was treated with 2N-isopropanol in toluene, and after 10 minutes warmed to 0°-2° C. and treated with 1 ml of water, 2 g of anhydrous sodium sulfate and 2.5 g of celite, then filtered. The filtrate was evaporated to dryness under vacuum to give 1.05 g of 5β-(2'-chloro3'S-hydroxy-4'(S,R)-methyl-5'-cyclopentyl-pent-1'-trans-1'-enyl)-2α,4α-dihydroxy-cyclopentane-1α-ethanal-γ-lactol-3',4-bis-DIOX-ether.

EXAMPLE 43

Following the procedure described in example 42, 0.57 g of 5β-(2'-bromo-3'S-hydroxy-5'-cyclohexyl-pent-1'-trans-1'-enyl)-2α,4α-dihydroxy-cyclopentane-1α-acetic acid-γ-lactone-3'S,4-bis-THP-ether was reacted with 4.4 ml of 0.5 M DIBA solution to give 0.57 g of 5β-(2'-bromo-3'S-hydroxy-5'-cyclohexyl-pent-1'-trans-1'-enyl)-2α,4α-dihydroxy-cyclopentane-1α-ethanal-γ-lactol-3'S,4-bis-THP-ether.

EXAMPLE 44

Under nitrogen, a mixture of a 70% solution of sodium bis-(2-methoxyethoxy)-aluminium hydride in benzene (0.58 ml) and toluene (4 ml) was added dropwise to a stirred solution of 0.68 g of 5β-(2'-bromo-3'S-hydroxy-5'-(2'' -tetrahydrofuryl)-pent-1'-trans-1'-enyl)-2α,4α-dihydroxy-cyclopentane-1α-acetic acid-γ-lactone-3',4-bis-THP-ether in 25 ml of anhydrous toluene, cooled to −60° to −65° C.

Stirring was continued for 3 hours, then the excess reagent was destroyed by careful addition of 5% acetone in toluene. After 10 minutes, the mixture was warmed to 0°-2° C., treated with a saturated solution of NaH$_2$PO$_4$ (3 ml) and the crystalline precipitate filtered out. The filtrate was evaporated to dryness in vacuo to give 0.66 g of 5β-(2'-bromo-3'S-hydroxy-5'-(2''-tetrahydrofuryl)-pent-1'-trans-1'-enyl)-2α,4α-dihydroxy-cyclopentane-1α-ethanal-γ-lactol-3'S,4-bis-THP-ether. 0.4 g of this compound was treated in acetone (8 ml) with 4 ml of 0.2N oxalic acid and refluxed for 90 minutes; the solvent was removed under vacuum and the aqueous phase extracted with ethyl acetate. The combined organic extracts were washed with saturated ammonium sulfate until neutral, dried and evaporated to dryness.

The residue was chromatographed on silica gel, eluted with cyclohexane-diethyl acetate 70:30 to yield 0.25 g of pure 5β-(2'-bromo-3'S-hydroxy-5'-(2''-tetrahydrofuryl)-pent-1'-trans-1'-enyl)-2α,4α-dihydroxy-cyclopentane-1α-ethanal-γ-lactol.

EXAMPLE 45

Starting from one of the cyclopentane-1α-acetic acid-γ-lactone-3',4-bis-acetalic ethers (3',4-bis-THP-ethers and 3',4-bis-DIOX-ethers) listed in example 41, by reduction of the γ-lactone group with DIBA, according to the procedure given in examples 42 and 43 or with sodium bis-(2-methoxyethoxy)-aluminium hydride, as described in example 41, the 3',4-bis-acetalic ethers (3',1-bis-THP-ethers and 3',4-bis-DIOX-ethers) of the following 2α,4α-dihydroxy-cyclopentane-1α-ethanal-γ-lactols were obtained:

5β-(2'-chloro-3'S-hydroxy-4'(S,R)-methyl-5'-cyclopentyl)-pent-1'-trans-1'-enyl);

5β-(2'-chloro-3'S-hydroxy-5'-cyclopentyl)-pent-1'-trans-1'-enyl);

5β-(2'-bromo-3'S-hydroxy-5'-cyclohexyl-pent-1'-trans-1'-enyl);

5β-(2'-bromo-3'S-hydroxy-4'(S,R)-methyl-5'-cyclohexyl-pent-1'-trans-1'-enyl);

5β-(2'-bromo-3'S-hydroxy-4'S-methyl-5'-cyclohexyl-pent1'-trans-1'-enyl);

5β-(2'-bromo-3'S-hydroxy-4'R-methyl-5'-cyclohexyl-pent-1'-trans-1'-enyl);

5β-(2'-bromo-3'S-hydroxy-5'-(2''-nor-bornyl)-pent-1'-trans-1'-enyl);

5β-(2'-bromo-3'S-hydroxy-5'-(2'''-tetrahydrofuryl)-pent-1'-trans-1'-enyl);

5β-(2'-bromo-3'S-hydroxy-5'-(2'''-tetrahydrothiophenyl)-pent-1'-trans-1'-enyl);

5β-(2'-bromo-3'S-hydroxy-5'-(adamantyl)-pent-1'-trans-1'enyl);

5β-(2'-bromo-3'S-hydroxy-5'-bicyclo[2,2,2]octyl-pent-1'-trans-1'-enyl);

5β-(2'-bromo-3'S-hydroxy-5'-cycloheptyl)-pent-1'-trans-1'enyl);

5β-(2'-bromo-3'S-hydroxy-5'-cyclopropyl-pent-1'-trans-1'-enyl);

5β-(2'bromo-3'S-hydroxy-5'-(4''-tert-butyl)-cyclohexyl-pent-1'-trans-1'-enyl);

5β-(2'-bromo-3'S-hydroxy-5'-cyclopentyl-pent-1'-trans-1'-enyl);

5β-(2'-bromo-3'S-hydroxy-4'S-methyl-5'-cyclopentyl-pent-1'-trans-1'-enyl);

5β-(2'-bromo-3'5-hydroxy-4'R-methyl-5'-cyclopentyl-pent-1'-trans-1'-enyl);

5β-(2'-bromo-3'S-hydroxy-4'-cyclohexyl-butyl-1'-trans-1'-enyl);

5β-(2'-bromo-3'S-hydroxy-4'-cyclopentyl-but-1'-trans-1'-enyl);

5β-(2'-bromo-3'S-hydroxy-4'-adamantyl-but-1'-trans-1'-enyl);

5β-(2'-bromo-3'S-hydroxy-6'-cyclohexyl-hex-1'-trans-1'enyl);

and their 3'R-epimeric alcohols, as the 3',4-bis-THP-ethers and the 3',4-bis-DIOX-ethers that, when desired, were deacetalated in acetone-0.2N oxalic acid to give the 3',4-free diols.

EXAMPLE 46

A solution of 2.6 g of 5β-hydroxymethyl-2α,4α-dihydroxy-cyclopentane-1α-acetic acid-γ-lactone-4-p-phenylbenzoate in 38 ml of benzene-DMSO (75:25) was reacted with 4.6 g of dicyclohexylcarbodiimide and 7.5 ml of a solution of trifluoroacetate of pyridine (2 ml of pyridine—1 ml of trifluoroacetic acid in 25 ml of benzene:DMSO 75:25).

After 3 hours, the excess reagent was destroyed by reaction with 2.8 g of oxalic acid in 6 ml of methanol, then diluted with 80 ml of water and 80 ml of benzene. After filtration, the filtrate was washed until neutral, dried and concentrated under vacuum to 15 ml (solution of the aldehyde).

To a suspension of 334 mg of 80% sodium hydride in 80 ml of benzene was added dropwise a solution of 3.92 g of dimethyl-(2-oxo-4-cyclohexyl)-butyl-phosphonate in 15 ml of benzene. This was stirred for 2 hours, then the solution of aldehyde was added. After an additional 20 minutes of stirring, the mixture was filtered and the filtrate washed with 5% $NaH_2PO_4$ and sodium chloride until neutral, then evaporated to dryness. After crystallization from hexane, 2.38 g were obtained of 5β-(2'-oxo-5'-cyclohexyl-pent-1'-trans-1'-enyl)-2α, 4α-dihydroxy-cyclopentane-1α-acetic acid-γ-lactone-4-p-phenylbenzoate, m.p. 104°–106° C.

Two g of this compound were dissolved in 20 ml of dimethoxy ethane and 40 ml of ethyl ether and added dropwise to 250 ml of 0.05M zinc borohydride in ethyl ether. After 30 minutes, the excess reagent was destroyed with 2N sulfuric acid. The organic phase was separated, washed until neutral and evaporated to dryness to give 2.1 g of crude 5β-(3'(S,R)-hydroxy-5'-cyclohexyl-pent-1'-trans-1'-enyl)-2α,4α-dihydroxy-cyclopentan-1α-acetic acid-γlactone-4-p-phenylbenzoate.

This compound was dissolved in 30 ml of anhydrous THF and reacted with 4.78 g of pyrrolidone-2-hydrotribromide, overnight at room temperature, with constant stirring. It was diluted with 120 ml of ethyl ether, filtered and the filtrate washed with saturated ammonium sulfate until neutral. After drying over $MgSO_4$, it was evaporated in vacuo on a water bath less than 40° C. The crude 5β-(1'ξ,2'ξ-dibromo-3'(S,R)-hydroxy-5'-cyclohexyl-pentanyl)-2α,4α-dihydroxy-cyclopentan-1α-acetic acid-γ-lactone-4-p-phenylbenzoate (about 3 g) was dissolved in 150 ml of acetone, cooled to 0° and oxidized by addition of 8.2 ml of Jones' reagent. After 5 minutes, it was diluted with 7 volumes of benzene and washed until neutral with a saturated ammonium sulfate solution, dried on $MgSO_4$ and concentrated under vacuum to ½ volume. Then 2.5 ml of triethylamine were added and it was left overnight at room temperature. The mixture was washed with 40% citric acid solution (3 times 8 ml), than with ammonium sulfate until neutral, then dried and evaporated to give 2.6 g of crude product which was crystallized from ethyl ether to give 1.2 g of 5β-(2'-bromo-3'-oxo-5'-cyclohexyl-pent-1'-trans-1'-enyl)-2α,4α-dihydroxy-cyclopentane-1α-acetic acid-γ-lactone-4-p-phenylbenzoate, m.p. 154°–156° C.

EXAMPLE 47

Sulfonyl chloride (13.5 ml) was added dropwise, with constant stirring to a solution of 4.8 g of 5β-(3'-oxo-5'-cyclohexyl - pent - 1'-trans-1'-enyl)-2α,4α-dihydroxycyclopentane-1α-acetic acid-γ-lactone-4-p-phenylbenzoate in 95 ml of anhydrous pyridine, cooled to 0°–5° C. and the stirring continued at 0°–2° for 16 hours. The reaction mixture was then poured into cold 2N $H_2SO_4$ (500 ml) and extracted many times with ethyl acetate.

The combined organic extracts were washed with 4N $H_2SO_4$, water, 5% $NaHCO_3$ and water until neutral, dried over $MgSO_4$ and evaporated to dryness under vacuum. The crude residue (4.82 g) was purified by chromatography through a short silica gel column (40 g). Elution with $CH_2Cl_2$ gave pure 5β-(2'-chloro-3'-oxo-5'-cyclohexyl-pent-1'-trans-1'-enyl)-2α,4α-dihydroxy-cyclopentane-1α-acetic acid-γ-lactone-4-p-phenylbenzoate (2.96 g).

EXAMPLE 48

Using the procedure described in example 46, by reaction of 5β-formyl-2α,4α-dihydroxy-cyclopentane-1α-acetic acid-γ-lactone-i-p-phenylbenzoate with the sodium salts of the following phosphonates:
dimethyl-(2-oxo-3-cyclohexyl)-propyl-phosphonate and
dimethyl-(2-oxo-5-cyclohexyl)-pentyl-phosphonate, there were prepared respectively:
5β-(3'-oxo-4'-cyclohexyl-but-1'-trans-1'-enyl)-2α,4α-dihydroxy-cyclopentane-1α-acetic acid-γ-lactone-4-p-phenylbenzoate, m.p. 140°–142°, $[α]_D = -128°$ ($CHCl_3$) and
5β-(3'-oxo-6'-cyclohexyl-hex-1'-trans-1'-enyl)-2α,4α-dihydroxy-cyclopentan-1α-acetic acid-γ-lactone-4-p-phenylbenzoate, m.p. 92°–93° C., $[α]_D = -118°$ C. ($CHCl_3$).

EXAMPLE 49

A solution of 300 mg of 5β-(3'-oxo-6'-cyclohexyl-hex-1'-trans-1'-enyl)-2α,4α-dihydroxy-cyclopentan-1α-acetic acid-γ-lactone-4-p-phenylbenzoate in 6 ml of anhydrous tetrahydrofuran was mixed with 360 mg of pyrrolidone hydrotribromide and maintained for 3 hours with constant stirring, then diluted with 20 ml of benzene. After filtration, the filtrate had 0.25 ml of triethylamine added and it was maintained at 25°–28° C. for 2 hours, after which it was washed with 1N $H_2SO_4$ and water until neutral.

It was dried and evaporated to dryness to give 0.35 g of crude product. After crystallization from MeOH/$CH_2Cl_2$, 280 mg were obtained of 5β-(2'-bromo-3'-oxo-6'-cyclohexyl-hex-1'-trans-1'-enyl)-2α,-4α-dihydroxy-cyclopentan-1α-acetic acid-γ-lactone-4-p-phenylbenzoate, m.p. 148°–149° C., $[α]_D = -96°$ ($CHCl_3$).

The same compound was also obtained by a completely independent procedure as described below:

To a suspension of 60 mg of 80% NaH in 8 ml of benzene, a solution of 0.553 g of dimethyl-(2-oxo-5-cyclohexyl)-pentyl-phosphonatc in 5 ml of benzene was added dropwise. When all the hydrogen had evolved, to the suspension of the carbanion of the phosphonate prepared in this way was added all at once 0.365 g of N-bromo-succinimide. This was stirred for 20 minutes and then a solution of 0.35 g of 5β-formyl-2α,4α-dihydroxy-cyclopentane-1α-acetic acid-γ-lactone-4-p-phenylbenzote in 10 ml of benzene was added and stirring continued for 30 minutes.

The organic phase was washed until neutral with water, dried and the solvent evaporated off. After crystallization from methanol, 0.36 g were obtained of 5β-(2'-bromo-3'-oxo-6'-cyclohexyl-hex-1'-trans-1'-enyl)-2α,4α-dihydroxy-cyclopentane-1α-acetic acid-γ-lactone-4p-phenylbenzoate, m.p. 148°–149° C.

The mother liquors from the two different synthesis were combined and evaporated to dryness for separation by thin layer chromatography (silica gel developed in methylene chloride-ethyl ether 96:4).

An additional 90 mg of the transenone and 50 mg of the isomer 5β-(2'-bromo-3'-oxo-6'-cyclohexyl-hex-1'-cis-1'-enyl)-2α,4α-dihydroxy-cyclopentane-1α-acetic acid-γ-lactone-4-p-phenylbenzoate, m.p. 129°–131° C., were obtained. The compounds were identified on the basis of NMR spectra.

Trans derivative: $H_1$, 6.94 δ, J=9 Hz.
Cis derivative: $H_1$, 6.18 δ, $J_{AB}$=9 Hz.

EXAMPLE 50

Using the procedures outlined in example 49, starting from 5β-(3′-oxo-4′-cyclohexyl-but-1′-trans-1′-enyl)-2α,-4α-dihydroxy-cyclopentan-1α-acetic acid-γ-lactone-4-p-phenylbenzoate, by addition of bromine followed by dehydrohalogenation and by direct synthesis (that is alkylation), of the 5β-formyl-2α,4α-dihydroxy-cyclopentane-1α-acetic acid-γ-lactone-4-p-phenylbenzoate with the carbanion of dimethyl-(1-bromo-2-oxo-3-cyclohexyl)-propyl-phosphonate generated in situ, we prepared 5β-(2′-bromo-3′-oxo-4′-cyclohexyl-but-1′-trans-1′-enyl)-2α,4α-dihydroxy-cyclopentane-1α-acetic acid-γ-lactone-4-p-phenylbenzoate, m.p. 181°–182° C., $[α]_D$= −90.7° (CHCl$_3$).

$H_1$, 6.98 δ, $J_{AB}$=9 Hz, and from the mother liquors the cis-isomer was isolated, m.p. 149°–149.5° C., $[α]_D$= −192° (CHCl$_3$), $H_1$=6.18 δ, $J_{AB}$=10.2 Hz.

We claim:
1. An optically active or racemic prostaglandin of the formula:

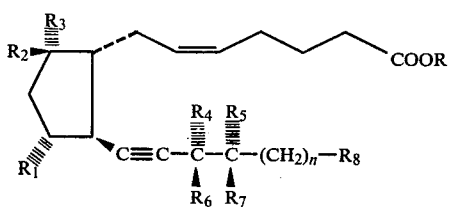

wherein:
R is a hydrogen atom, $C_1$–$C_{12}$ alkyl group or a cation of a pharmaceutically acceptable base;
$R_1$ is hydroxy;
$R_2$ is hydrogen and $R_3$ is hydroxy, a lower alkanoyloxy group or a benzoyloxy group;
one of $R_4$ and $R_5$ is hydroxy and the other is hydrogen;
$R_6$ and $R_7$ are independently hydrogen or $C_1$–$C_4$ alkyl;
n is zero, 1, 2 or 3;
$R_8$ is the radical

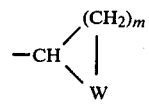

wherein
m is 1, 2, 3, 4 or 5 and
W is an oxygen atom, a sulphur atom or
wherein $R_9$ is hydrogen or a $C_1$ alkyl, or $R_8$ is 1-adamantyl or 2-nor-bornyl and the pharmaceutically acceptable esters and salts thereof.

2. The compound 5c-9α,11α,15S-trihydroxy-20,19,18-trinor-17-(2′-nor-bornyl)-prost-5-en-13-ynoic acid and the pharmaceutically acceptable salts thereof.

3. The compound 5c-9α,11α,15S-trihydroxy-20,19,18-trinor-17-(1′-adamantyl)-prost-5-en-13-ynoic acid and the pharmaceutically acceptable salts thereof.

4. The compound 5c-9α,11α,15S-trihydroxy-18,19,20-trinor-17-(2′-tetrahydrofuryl)-prost-5-en-13-ynoic acid and the pharmaceutically acceptable salts thereof.

5. The compound 5c-9α,11α,15S-trihydroxy-18,19,20-trinor-17-(2′-tetrahydrothiophenyl)-prost-5-en-13-ynoic acid and the pharmaceutically acceptable salts thereof.

6. A pharmaceutical composition having luteolytic abortifacient or labor-inducing activity comprising, as the active ingredient, an effective amount of the compound of claim 1 together with a pharmaceutically acceptable carrier or diluent.

* * * * *

UNITED STATES PATENT AND TRADEMARK OFFICE
CERTIFICATE OF CORRECTION

PATENT NO. : 4,169,145

DATED : September 25, 1979

INVENTOR(S) : Carmelo Gandolfi, et al

It is certified that error appears in the above-identified patent and that said Letters Patent are hereby corrected as shown below:

In the heading: the second line of paragraph [30] should read --Sep. 25, 1974  Italy  27654/74--.

Column 1, line 20, in the formula (I) correct "$R_1$" opposite $R_5$ to read --$R_4$--;

Column 1, lines 34, 36 and 38 and Column 2, line 18 correct "symbol---" to read --symbol===--.

Column 40, rewrite lines 1-20 as follows:

$R_2$ is hydrogen and $R_3$ is hydroxy, a lower alkanoyloxy group or a benzoyloxy group;

one of $R_4$ and $R_6$ is hydroxy and the other is hydrogen;

$R_5$ and $R_7$ are independently hydrogen or $C_1$-$C_4$ alkyl;

UNITED STATES PATENT AND TRADEMARK OFFICE
CERTIFICATE OF CORRECTION

PATENT NO. : 4,169,145
DATED : September 25, 1979
INVENTOR(S) : Carmelo Gandolfi, et al It is certified that error appears in the above-identified patent and that said Letters Patent are hereby corrected as shown below:

n is zero 1, 2 or 3;

$R_8$ is the radical

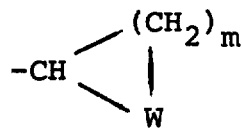

wherein m is 1, 2, 3, 4 or 5 and

W is an oxygen atom, a sulphur atom or $>NR_9$ wherein $R_9$ is hydrogen or a $C_1$-$C_4$ alkyl, or $R_8$ is 1-adamantyl or 2-nor-bornyl and the pharmaceutically acceptable esters and salts thereof.

Signed and Sealed this

Eighteenth Day of March 1980

[SEAL]

Attest:

SIDNEY A. DIAMOND

Attesting Officer — Commissioner of Patents and Trademarks